United States Patent [19]

Mase et al.

[11] Patent Number: 5,180,730
[45] Date of Patent: Jan. 19, 1993

[54] HETEROCYCLIC COMPOUNDS

[75] Inventors: Toshiyasu Mase, Chiba; Ryuji Tsuzuki, Tokyo; Hiromu Hara, Saitama; Kiyoshi Murase, Saitama; Kenichi Tomioka, Saitama, all of Japan

[73] Assignee: Yamanouchi Pharmaceutical Co., Ltd., Tokyo, Japan

[21] Appl. No.: 682,867

[22] Filed: Apr. 5, 1991

Related U.S. Application Data

[60] Continuation of Ser. No. 491,356, Mar. 9, 1990, abandoned, which is a division of Ser. No. 228,542, Aug. 4, 1988, Pat. No. 4,933,348, which is a division of Ser. No. 885,085, Jul. 14, 1986, Pat. No. 4,803,211.

[30] Foreign Application Priority Data

Jul. 22, 1985 [JP] Japan .................................. 60-164267
Oct. 7, 1985 [JP] Japan .................................. 60-224197
Dec. 26, 1985 [JP] Japan .................................. 60-297097

[51] Int. Cl.⁵ .................... C07D 213/62; A61K 31/44
[52] U.S. Cl. .................................. 514/348; 546/296; 546/297; 546/298
[58] Field of Search .................. 546/297, 297, 298; 514/348

[56] References Cited

FOREIGN PATENT DOCUMENTS 132366   1/1985  European Pat. Off. .
181779   5/1986  European Pat. Off. .
1555753  11/1979 United Kingdom .
2058785  4/1988  United Kingdom .

Primary Examiner—Robert Gerstl
Attorney, Agent, or Firm—Burgess, Ryan Wayne

[57] ABSTRACT

This invention relates to novel heterocyclic compounds structurally characterized by containing a specific heterocyclic group and by the presence of —CH$_2$—S— directly bound to the specific heterocyclic group. These heterocyclic compounds are useful as medicines, particularly as antagonists of SRS-A (slow reacting substance of anaphylaxis).

5 Claims, No Drawings

HETEROCYCLIC COMPOUNDS

This application is a continuation of application Ser. No. 491,350, filed Mar. 9, 1990 now abandoned, which is a divisional of U.S. 228,542 filed Aug. 4, 1988, now U.S. Pat. No. 4,933,348 which is a divisional of U.S. 885,085 filed Jul. 14, 1986 now U.S. Pat. No. 4,803,211.

This invention relates to heterocyclic compounds represented by general formula (I) described below or salts thereof which are useful as medicines, particularly as antagonists of SRS-A (slow reacting substance of anaphylaxis):

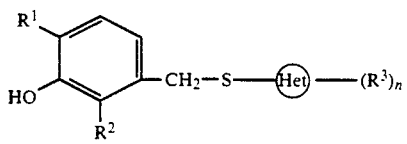

wherein $R^1$ represents a lower acyl group; $R^2$ represents a lower alkyl group; (Het) represents a 5- or 6-membered heterocyclic ring which contains 1 to 3 nitrogen atoms and may additionally contain a sulfur atom or an oxygen atom; $R^3$ represents a carboxy group, an amino group, a lower alkylamino group which may be carboxy-substituted, a lower alkanoylamino group which may be carboxy-substituted, a di-lower alkylamino group, a hydroxy group, a lower alkoxy group which may be carboxy-substituted, a mercapto group, a lower alkylthio group which may be carboxy-substituted, a group represented by formula:

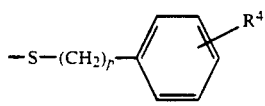

or formula:

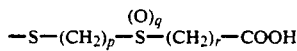

(wherein p represents an integer of 1 to 5, q represents 0, 1 or 2, r represents an integer of 1 to 5; $R^4$ represents a carboxy group, a lower alkoxy group which may be carboxy-substituted or, a lower alkyl group which may be carboxy-substituted and contain a sulfur atom or an oxygen atom in the carbon chain thereof); and n represents 0 or an integer of 1, 2 or 3; provided that when the compound is substituted by a carboxy group, said carboxy group may be in the form of an ester and, when n represents an integer of 2 or 3, $R^3$ may be a group different from each other.

It is generally considered that in allergic asthma and other atopic diseases of human or anaphylactic shock in animals, various chemical mediators are released from the lung and other tissues and cause difficulties in the living body, such as contraction of smooth muscles, e.g., bronchi, pulmonary artery, etc., and enhancement of vascular permeability in the skin. As such chemical mediators, there are histamine and SRS-A. Histamine plays an important role in guinea-pig anaphylactic shock but not in allergic asthma in human [Eiser, "Pharmacology and Therapeutics", 17, 239-250 (1982)]. On the other hand, some evidence suggests that SRS-A is the most important chemical mediator of allergic asthma in human [Brocklehurst, "Journal of Physiology", 151, 416-435 (1960); Austen and Orange, "American Review of Respiratory Diseases", 12, 423-436 (1975); Adams and Lichtenstein, "Journal of Immunology", 122, 555-562 (1979)].

The development of medicaments for prophylaxis, elimination and reduction of hypersensitivity reactions has aimed at inhibiting the production and release of such chemical mediators or antagonizing the action of these chemical mediators. As an inhibitor of histamine release, disodium cromoglycate is well known and as antagonists of actions induced by histamine, various anti-histaminics are commercially available. SRS-A is known as a slow reactive and long acting chemical mediator while histamine is a rapid acting and short acting chemical mediator. It has recently been recognized that SRS-A is a mixture of Leukotrienes $C_4$, $D_4$ and $E_4$, the structure of which have been determined by Samuelsson. SRS-A, i.e., Leukotrienes are lipoxygenase metabolites of polyvalent unsaturated fatty acids (in particular, arachidonic acid) and it has been reported that SRS-A has various activities such as enhancement of mucus secretion, reduction of mucociliary transport, coronary artery contraction, reduction of cardiac contractibility, etc., in addition to the aforesaid action as chemical mediator in immediate hypersensitivity reactions. Accordingly, it has been desired to develop medicaments capable of inhibiting the production and release of SRS-A or antagonizing the effects of SRS-A.

The present inventors have extensively investigated medicaments capable of inhibiting the production and release of SRS-A or medicaments capable of antagonizing the effects of SRS-A. As a result, they have found that the aforesaid compounds (I) of this invention strongly antagonize SRS-A and have thus accomplished this invention.

The characteristic feature of the compounds according to this invention in terms of chemical structure resides in that the 5- or 6-membered heterocyclic group which contains 1 to 3 nitrogen atoms and may additionally contain a sulfur atom or an oxygen atomis bound. Namely, the compounds of this invention represented by formula (I):

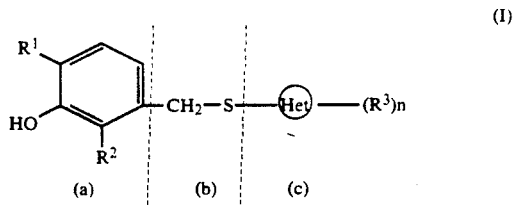

are characterized by the chemical structure that moiety (c) is the aforesaid specific heterocyclic group and this specific heterocyclic group is directly bonded to moiety (b).

A variety of compounds are heretofore known in relation to the compounds of this invention. For example, the compounds described in EP-A-181779 by this applicant are different from those of this invention in that a moiety corresponding to moiety (b) is —O—A—Y—, unlike —CH$_2$—S— in the compounds of this invention. Compounds containing moiety (a) having directly bonded thereto moiety (b) are known in Published Unexamined Japanese Patent Application 48944/85. The claims encompass compounds containing moiety (b) to which a moiety corresponding to moiety (c) is directly bound. However, compounds specifically prepared all contain moiety (b) having bonded thereto a moiety corresponding to moiety (c) via a phenylene group

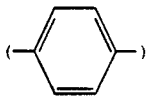

or an alkylene group (—(CH$_2$)$_n$—) but, no compound containing any direct bond between the two moieties is disclosed therein. Further in the Japanese patent application the moiety corresponding to moiety (c) is limited to a 5-tetrazole group

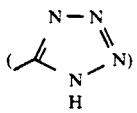

in case that the moiety corresponding to moiety (c) represents a heterocyclic group. That is, any concrete compound containing moiety (b) having directly bonded thereto moiety (c) was unknown at the time when this application was filed. The compound containing moiety (b) having directly bonded thereto the moiety corresponding to moiety (c) merely as a general concept but the moiety corresponding to moiety (c) is limited to the 5-tetrazole group. Therefore, the compounds of this invention are unknown not only concretely but as a general concept.

The symbols used for the compounds of this invention represented by formula (I) are explained below in more detail.

The term "5- or 6-membered heterocyclic group which contains 1 to 3 nitrogen atoms and may additionally contain a sulfur atom or an oxygen atom" refers to a 5- or 6-membered monocyclic heterocyclic group which necessarily contains 1 to 3 nitrogen atoms and may additionally contain a sulfur atom or an oxygen atom.

Representative examples of hetero rings which constitute these heterocyclic group include pyrrole, imidazole, triazole, oxazole, thiazole, isothiazole, oxadiazole, thiadiazole, pyridine, pyrazine, pyrimidine, 1,3,5-triazine, pyrrolidine, piperidine and morpholine. These hetero rings may have 1 to 3 substituents shown by R$^3$ on any optional carbon atom(s) or nitrogen atom(s).

The term "lower" refers to a straight or branched carbon chain having 1 to 8 carbon atoms Accordingly, the "lower alkyl group" includes a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, a heptyl group, a 1-methylhexyl group, a 1-ethylpentyl group, a 6-methylhexyl group, an octyl group, etc.

Examples of the "lower acyl group" include a formyl group, an acetyl group, a propionyl group, a butyryl group, an isobutyryl group, a valeryl group, an isovaleryl group, a pivaloyl group, a hexanoyl group, etc.

The term "lower alkyl which may be carboxy-substituted" or "lower alkanoyl which may be carboxy-substituted" refers to a lower alkyl group or a lower alkanoyl group which may optionally have a carboxy group as a substituent on the alkyl groups exemplified for the above-described lower alkyl group or the corresponding alkanoyl group. Examples of the "lower alkoxy group which may be carboxy-substituted" or "lower alkylthio group which may be carboxy-substituted" include a methoxy- or methylthio group, an ethoxy- or ethylthio group, a propoxy- or propylthio group, an iso- propoxy- or isopropylthio group, a n-butoxy- or n-butylthio group, a carboxymethoxy- or carboxymethylthio group (—S—CH$_2$COOH), a 3-carboxypropoxy- (—OCH$_2$CH$_2$CH$_2$—COOH) 3-carboxypropylthio group (—S—CH$_2$CH$_2$CH$_2$COOH), a 2-carboxy propoxy-

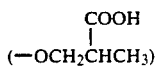

or 2-carboxypropylthio group

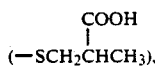

etc. Examples of the "lower alkylamino group which may be carboxy-substituted" include a methylamino group (—NHCH$_3$), an ethylamino group (—NHCH$_2$CH$_3$), a propylamino group (—NHCH$_2$CH$_2$CH$_3$), a carboxymethylamino group (—NHCH$_2$COOH), etc. Examples of the "lower alkanoylamino group which may be carboxy-substituted" include a formylamino group, an acetylamino group, a propionylamino group, an oxaloamino group (—NH-COCOOH), a carboxyacetylamino group (—NH-COCH$_2$COOH), a 3-carboxypropionylamino group (—NHCOCH$_2$CH$_2$COOH), etc.

The term "lower alkyl group which is carboxysubstituted and may contain a sulfur atom or an oxygen atom in the carbon chain thereof" shown by R$^4$ is a straight or branched carbon chain having 1 to 6 carbon atoms which may be substituted by a carboxy group at the carbon chain thereof and optionally contains an oxygen atom or a sulfur atom at the terminal or middle position of the carbon chain. Representative examples of the groups included in the definition are as follows:
carboxymethoxy group (—OCH$_2$COOH),
carboxymethylthio group (—SCH$_2$COOH),
1-carboxyethoxy group (—OCHCOOH),

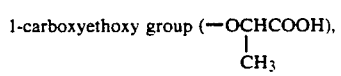

2-carboxyethyl group (—CH$_2$CH$_2$COOH),
carboxymethylthiomethyl group (—CH$_2$SCH$_2$COOH),
carboxymethoxymethyl group (—CH$_2$OCH$_2$COOH),
3-carboxypropoxy group (—OCH$_2$CH$_2$CH$_2$COOH),
2-carboxypropoxy group

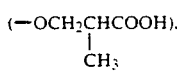

5-carboxypentyloxy group (—O(CH$_2$)$_5$COOH),
3-(carboxymethylthio)propyl group (—(CH$_2$)$_3$SCH$_2$COOH),
2-(2-carboxyethylthio)ethyl group (—(CH$_2$)$_2$S(CH$_2$)$_2$COOH),
3-(2-carboxyethylthio)propyl group (—(CH$_2$)$_3$S(CH$_2$)$_2$COOH)

These groups shown by R$^4$ may be substituted at any optional position on the phenyl ring.

Next, p and r each represents an integer of 1 to 5. Therefore, (CH$_2$)$_p$ and (CH$_2$)$_r$ each represents a methylene group, an ethylene group, a propylene group, a tetramethylene group (butylene group) or a pentamethylene group.

Further

can be a thio group (—S—, q=0), a sulfinyl group

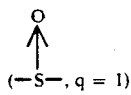

or a sulfonyl group

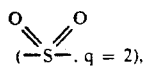

depending upon the number of q. Representative examples of the group

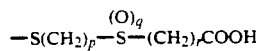

include the following:

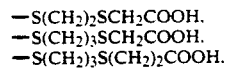

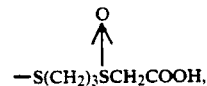

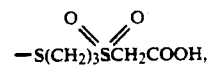

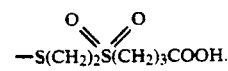

The compounds of this invention are described hereinabove wherein those having a carboxy group as a substituent may form esters or salts thereof. The compounds of this invention also include these esters or salts. Examples of the esters include lower alkyl esters such as a methyl ester, an ethyl ester, a propyl ester, etc. and further phenyl-lower alkyl esters which may optionally be substituted with a lower alkoxy group, such as a benzyl ester, a p-methoxybenzyl ester, etc. Examples of the salts include salts with inorganic bases such as sodium, potassium, etc.; salts with organic bases such as ethylamine, propylamine, diethylamine, triethylamine, morpholine, diethanolamine, etc.

The compounds of this invention include optical isomers based on the existence of asymmetric carbon: tautomers based on the kind of heterocyclic ring or the presence of an oxo group, a hydroxy group, a thioxo group or a mercapto group. This invention includes all such isomers, individually and in any admixture of two or more of them.

The compounds (I) of this invention can be prepared, for example, by processes shown by the following reaction equations:

Process 1:

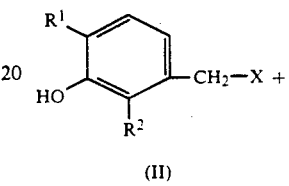

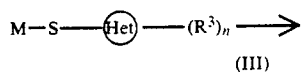

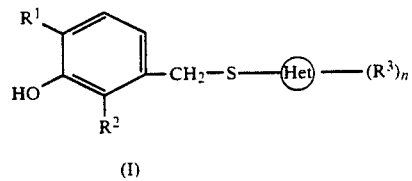

Process 2:

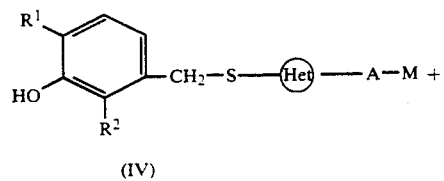

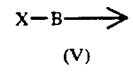

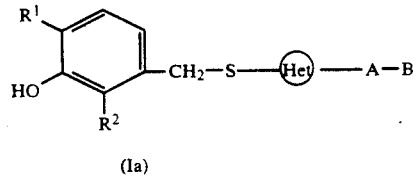

Process 3:

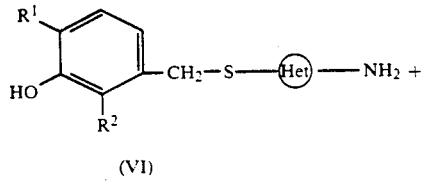

-continued

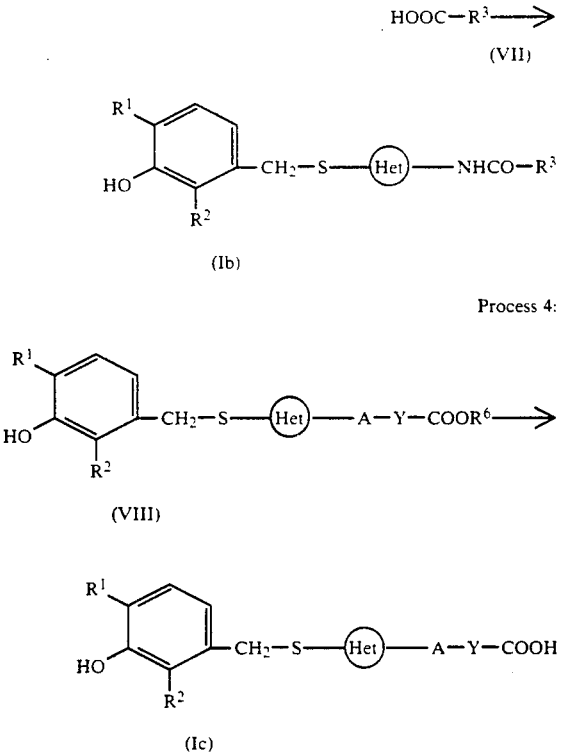

[wherein symbols represent the following significances:
(Het), R¹, R², R³, n: same as defined above
X: a halogen atom
M: a hydrogen atom or an alkali metal
A: an oxygen atom, a sulfur atom or an imino group (—NH—)
B: a lower alkyl group which may be carboxy-substituted, a lower alkanoyl group which may be carboxy-substituted or, a group shown by formula:

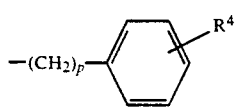

or formula:

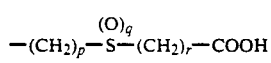

(wherein p, q, r and R⁴ have the same significances as defined above)
Y: a lower alkylene group, a lower alkanoyl group, a carbonyl group, or a group shown by formula:

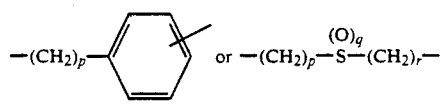

R⁵: a carboxy group or, a lower alkyl group which may be carboxy-substituted
R⁶: an ester residue (provided that the carboxy group may optionally take an ester form thereof when carboxy-substituted)

Process 1

A compound of this invention shown by general formula (I) is produced by reacting a substituted benzyl halide shown by general formula (II) with a mercapto-substituted heterocyclic compound or an alkali metal-substituted compound thereof shown by general formula (III).

The reaction can be performed using the compounds (II) and (III) in almost equimolar amounts, or with a slight excess of one, in an organic solvent such as dimethylformamide, dimethylsulfoxide, methanol, ethanol, propanol, acetone, methyl ethyl ketone, tetrahydrofuran, chloroform, dioxane, or the like.

When a mercapto-substituted heterocyclic compound is used as the compound (III), the reaction is generally performed in the presence of a base and suitable examples of such a base are potassium carbonate, Triton B, potassium hydroxide, sodium hydroxide, sodium hydride, etc. In order to accelerate the reaction, potassium iodide, bromo-tetra-n-butyl ammonium, etc. may also be added to the system, in a catalytic amount.

There is no particular restriction on the reaction temperature but the reaction is usually performed at room temperature or under heating.

Process 2

To perform this process, a compound (IV) which is a compound (I) of this invention wherein R³ is a hydroxy group, a mercapto group or an amino group is used as a starting material. An alkyl halide or an acyl halide (V) is reacted with the compound (IV). The reaction can be performed almost in a manner similar to Process 1.

Process 3

To perform this process, a compound (VI) wherein R³ is an amino group is acylated with a carboxylic acid (VII) or a reactive derivative thereof. As the reactive derivative of the carboxylic acid used in this case, there are an acid halide, an acid azide, an activated ester or an acid anhydride. When compound (VII) is used as a free carboxylic acid, it is advantageous to perform the reaction in the presence of a condensing agent such as dicyclohexylcarbodiimide, etc.

The reaction is performed using the compound (VI) and the compound (VII) or reactive derivative thereof in almost equimolar amounts, or with slight excess of one (e.g., the carboxylic acid component). When the carboxylic acid (VII) is used as a dicarboxylic acid (e.g., oxalic acid, malonic acid, etc.), the dicarboxylic acid is used in the form wherein either carboxy group is protected as an ester thereof, etc. As the reaction solvent, there are used those inert to this reaction such as pyridine, tetrahydrofuran, dioxane, etc.

Process 4

In this process, a compound (VIII) wherein R³ is an esterified carboxy group in the compounds (I) of this invention is de-esterified to give a compound (Ic) having a free carboxy group. In the de-esterification, there is adopted a method for performing hydrolysis in the presence of a base such as sodium carbonate, sodium hydroxide, etc. or, trifluoroacetic acid, hydrochloric acid, etc.

The compounds of this invention produced by these various processes can be isolated and purified by conventional operations such as extraction, recrystallization, column chromatography, etc.

The compounds (I) of this invention strongly antagonize the actions of SRS-A as described hereinbefore and hence are useful for the prophylaxis and treatment for various allergic diseases (for example, bronchial asthma, allergic rhinitis, urticaria), ischemic heart diseases, inflammations, etc. caused by SRS-A.

At least some compounds of this invention also inhibit the production and release of SRS-A and have bronchodilator action. Compounds of this invention may also be useful as anti-inflammatory or anti-ulcer agents.

(1) Inhibition of SRS-A- and $LTD_4$-induced contraction of guinea-pig ileum and trachea Methods: Male Hartley guinea-pigs, weighing 500 to 700 g were sacrificed by a blow on the head. The ileum and tracheal strips prepared according to the method of Constantine (Constantine, J. W., J. Pharm. Pharmacol., 17, 384 (1965)) were suspended with 1.0 g tension in an organ bath containing 10 ml of Tyrode solution equilibrated with a mixture of 95% $O_2$ and 5% $CO_2$ at 37° C. The tissues were equilibrated for 60 minutes; during this period the Tyrode solution was replaced every 15 minutes and the loading tension was adjusted to 1.0 g. The developed tension of the tissues was measured isometrically with a strain gauge transducer, and recorded on a Recticorder. Both the contractile response of the ileum to submaximal concentration of SRS-A (derived from guinea pig lung) and tracheal response to $10^{-8}M$ $LTD_4$ were recorded in the absence and then in the presence of various concentrations of test compounds. The incubation time of the compounds was 20 minutes.

Results: As shown in Table 1, many compounds of this invention showed very potent anti-SRS-A action in the isolated ileum. Furthermore, Compounds of Examples 2, 32, 33, 34, 35, 36, 37, 43 and 44 potently inhibited the contractions induced by $LTD_4$ in the isolated guinea pig trachea (Table 1).

TABLE 1

Anti-SRS-A and anti-$LTD_4$ effects of representative compounds of this invention in isolated guinea-pig ileum and trachea

| | IC 50 (M) | |
|---|---|---|
| Compound | Ileum Anti-SRS-A | Trachea Anti-$LTD_4$ |
| Example 2 | $4.2 \times 10^{-8}$ | $4.0 \times 10^{-8}$ |
| Example 4 | $4.1 \times 10^{-9}$ | — |
| Example 10 | $5.1 \times 10^{-8}$ | — |
| Example 11 | $9.1 \times 10^{-9}$ | — |
| Example 12 | $4.0 \times 10^{-9}$ | — |
| Example 13 | $2.1 \times 10^{-8}$ | — |
| Example 14 | $5.0 \times 10^{-8}$ | — |
| Example 22 | $2.2 \times 10^{-8}$ | — |
| Example 24 | $3.3 \times 10^{-9}$ | — |
| Example 32 | $1.5 \times 10^{-10}$ | $3.0 \times 10^{-9}$ |
| Example 33 | $2.9 \times 10^{-10}$ | $5.4 \times 10^{-8}$ |
| Example 34 | $1.1 \times 10^{-9}$ | $7.7 \times 10^{-8}$ |
| Example 35 | $1.1 \times 10^{-8}$ | $7.8 \times 10^{-9}$ |
| Example 36 | $1.1 \times 10^{-9}$ | $2.9 \times 10^{-9}$ |
| Example 37 | $3.6 \times 10^{-9}$ | $1.1 \times 10^{-8}$ |
| Example 43 | $4.7 \times 10^{-9}$ | $3.8 \times 10^{-9}$ |
| Example 44 | $4.5 \times 10^{-8}$ | $1.9 \times 10^{-7}$ |
| Example 46 | $3.1 \times 10^{-8}$ | — |

(2) Inhibition of $LTD_4$-enhanced vascular permeability in guinea-pig

Method: Male Hartley guinea-pigs weighing 270 to 305 g, starved for 16 hours, were intradermally injected 5 ng $LTD_4$ in a volume of 0.1 ml into two sites on the shaved back. In addition, 0.1 ml of vehicle was injected intradermally in each animal to see non-specific irritation. One ml of saline containing 1% Evans blue was intravenously injected 2 minutes before $LTD_4$ injection. Animals were sacrificed 30 minutes after $LTD_4$ injection. The leaked dye at the site of $LTD_4$ or vehicle injection was extracted according to the method of Harada et al. (Harada, M. et al., J. Pharm. Pharmacol., 23, 218 (1971)) and measured photometrically at 620 nm. The $LTD_4$-induced skin reaction was expressed as a difference in the amount of dye between $LTD_4$ and vehicle. Test compounds were orally administered 30 minutes before $LTD_4$ injection.

Results: Compounds of Examples 2, 34 and 37 dose-dependently inhibited the $LTD_4$-enhanced vascular permeability in guinea-pigs; their $ED_{50}$ values were 11.3, 4.2 and 7.0 mg/kg p.o., respectively. These results reveal that Compounds of Examples 2, 34 and 37 show potent anti-leukotriene effect by oral route.

(3) Acute toxicity in rats

Male Fischer 344 rats 7 week old were used. Compounds of Examples 2 and 37 at 1000 mg/kg p.o. caused no toxic effect upon the rats during the observation period for 14 days.

The compounds (I) of this invention can be orally or parenterally administered as they are or as medical compositions of these compounds and pharmaceutically acceptable carriers or excipients [e.g., tablets, capsules, powders, granules, pills, ointments, syrups, injections, inhalants, suppositories, etc.]. The dose may vary depending upon the patient, administration route, symptoms, etc but is usually 0.1 to 500 mg, preferably 1 to 200 mg, per adult per day orally or parenterally administered two or three times per day.

Hereafter this invention is illustrated in more detail by the following examples.

EXAMPLE 1

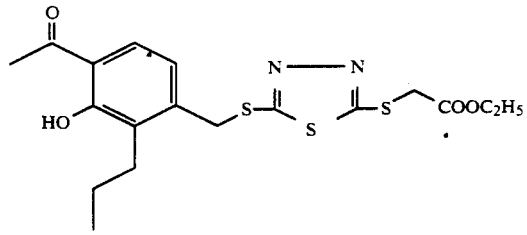

To a mixture of 0.42 g of 4-acetyl-3-hydroxy-2-propylbenzyl chloride, 0.54 g of ethyl [(5-mercapto-1,3,4-thiadiazol-2-yl)thio]acetate, 0.30 g of anhydrous potassium carbonate and 5 ml of methyl ethyl ketone were added catalytic amounts of potassium iodide and tetra-n-butylammonium bromide followed by stirring at 60° C. for 3 hours. The reaction mixture was diluted with toluene and insoluble matters were filtered off. The filtrate was washed with an aqueous sodium hydroxide solution and dried over anhydrous magnesium sulfate. The solvent was then distilled off. The residue was subjected to silica gel column chromatography. Elution with a mixture of hexane-ethyl acetate (5:1) gave 0.75 g of oily ethyl [[5-[(4-acetyl-3-hydroxy-2-propylbenzyl)-thio]1,3,4-thiadiazol-2-yl]thio]acetate. Nuclear magnetic resonance spectrum (in $CDCl_3$, TMS internal standard, ppm): 1.18 (t, 3H), 1.28 (t, 3H), 1.4–1.8 (2H), 2.60 (s, 3H), 2.6–2.8 (2H), 4.08 (s, 2H), 4.22 (q, 2H), 4.54 (s, 2H), 6.90 (d, 1H), 7.52 (d, 1H), 12.69 (s, 1H)

Mass spectrum m/z: 426 (M⁻)

EXAMPLE 2

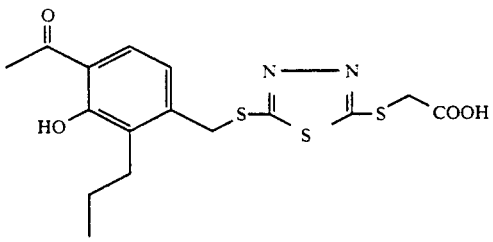

In 7.8 ml of 90% methanol was dissolved 0.98 g of ethyl [[5-[(4-acetyl-3-hydroxy-2-propylbenzyl)thio]-1,3,4- thiadiazol-2-yl]thio]acetate obtained in Example 1 with heating at 60° C. Further 6.1 ml of a 1N aqueous sodium hydroxide solution was added to the solution followed by stirring at 60° C. for 30 minutes. A 1N aqueous sodium hydroxide solution and ethyl acetate were added to the reaction mixture to fractionate. The aqueous phase was made acidic with a 1N hydrochloric acid and extracted with ethyl acetate. The extract was washed with, in sequence, water, a saturated aqueous sodium chloride solution and water and then, dried over anhydrous magnesium sulfate. The solvent was then distilled off. Recrystallization of the thus obtained solid from isopropyl alcohol gave 0.75 g of [[5-[(4-acetyl-3-hydroxy-2-propylbenzyl)thio]-1,3,4-thiadiazol-2-yl]thio]-acetic acid.

Melting point: 116°-118° C.

| Elemental analysis (as $C_{16}H_{18}N_2O_4S_3$) | | | | |
|---|---|---|---|---|
| | C (%) | H (%) | N (%) | S (%) |
| Calcd. | 48.22 | 4.55 | 7.03 | 24.14 |
| Found | 48.11 | 4.56 | 6.96 | 24.31 |

EXAMPLE 3

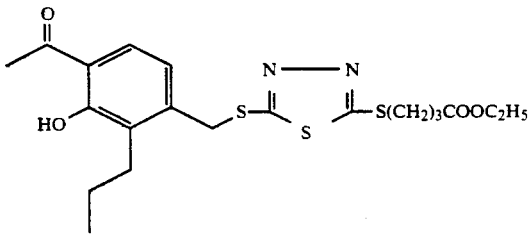

Using as starting materials 0.30 g of 4-acetyl-3-hydroxy-2-propylbenzyl chloride and 0.42 g of ethyl 4-[(5-mercapto-1,3,4-thiadiazol-2-yl)thio]butyrate, 0.59 g of. oily ethyl 4-[[5-[(4-acetyl-3-hydroxy-2-propylbenzyl)thio]-1,3,4-thiadiazol-2-yl]thio]butyrate was obtained in a manner similar to Example 1.

Nuclear magnetic resonance spectrum (in CDCl₃, TMS internal standard, ppm): 0.99(t,3H), 1.36(t,3H), 1.4-1.8(2H), 2.0-2.4(2H), 2.4-2.8(4H), 2.61(s,3H), 3.34(t,2H), 4.13(q,2H), 4.55(s,2H), 6.93(d,1H), 7.54(d,1H), 12.69(s,1H), Mass spectrum m/z: 454 (M⁻)

EXAMPLE 4

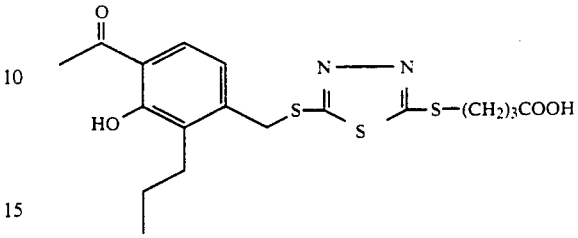

Using as a starting material 0.25 g of 4-[[5-[(4-acetyl-3-hydroxy-2-propylbenzyl)thio]-1,3,4-thiadiazol-2-yl]thio]butyrate obtained in Example 3, 0.23 g of 4-[[5-[(4-acetyl-3-hydroxy-2-propylbenzyl)thio]-1,3,4-thiadiazol-2-yl]thio]butyric acid was obtained in a manner similar to Example 2.

Melting point: 75°-78° C.

| Elemental analysis (as $C_{18}H_{22}N_2O_4S_3$) | | | | |
|---|---|---|---|---|
| | C (%) | H (%) | N (%) | S (%) |
| Calcd. | 50.68 | 5.20 | 6.57 | 22.55 |
| Found | 50.55 | 5.32 | 6.56 | 22.36 |

EXAMPLE 5

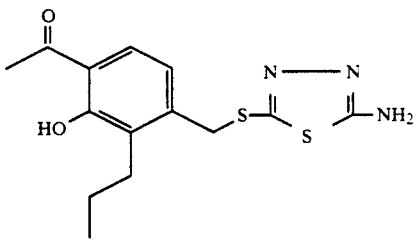

To a mixture of 0.30 g of 4-acetyl-3-hydroxy-2-propylbenzyl chloride, 0.22 g of 2-amino-5-mercapto-1,3,4-thiadiazole, 0.22 g of anhydrous potassium carbonate and 3 ml of methyl ethyl ketone were added catalytic amounts of potassium iodide and tetra-n-butylammonium bromide followed by stirring at 60° C. for 2 hours. Ethyl acetate was added to the reaction mixture. After insoluble matters were filtered off, the filtrate was washed with an aqueous sodium hydroxide solution and then dried over anhydrous magnesium sulfate The solvent was then removed by distillation to give 0.44 g of 2-amino-5-[(4-acetyl-3-hydroxy-2-propylbenzyl)thio]-1,3,4-thiadiazole.

Melting point 143°-147° C.

Nuclear magnetic resonance spectrum (in DMSO-d₆, TMS internal standard, ppm): 0.92(t,3H), 1.3-1.7(2H), 2.3-2.8(2H), 2.62(s,3H), 4.32(s,2H), 6.88(d,1H), 7.72(d,1H), 12.7(s,1H), Mass spectrum m/z: 323 (M⁺)

EXAMPLE 6

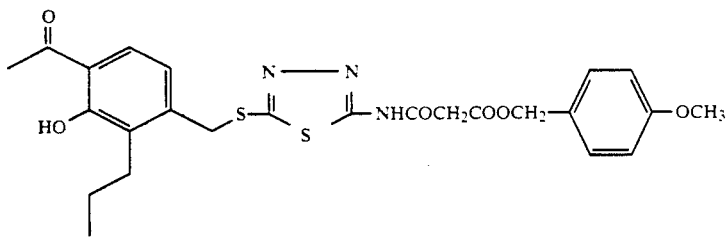

To a solution of 0.14 g of 2-amino-5-[(4-acetyl-3-hydroxy-2-propylbenzyl)thio]-1,3,4-thiadiazole obtained in Example 5 and 0.15 g of mono-p-methoxybenzyl malonate in 3 ml of pyridine were added 0.15 g of dicyclohexylcarbodiimide and a catalytic amount of p-toluenesulfonic acid. The resultant mixture was stirred at room temperature for hours. During the stirring, 0.15 g each of mono-p-methoxybenzyl malonate and dicyclohexylcarbodiimide were supplemented to the system. After completion of the reaction, ethyl acetate was added to the system. After insoluble matters were filtered off, the filtrate was concentrated under reduced pressure The obtained residue was dissolved in chloroform. The solution was washed with, in sequence, 1N hydrochloric acid, water, a saturated aqueous sodium bicarbonate solution and water and then, dried over anhydrous magnesium sulfate The solvent was then removed by distillation. The resultant residue was subjected to silica gel column chromatography followed by elution with a mixture of chloroform-methanol (4:1). The eluate was recrystallized from isopropyl alcohol to give 0.04 g of p-methoxybenzyl 3-[[5-[(4-acetyl-3-hydroxy-2-propylbenzyl)thio]-1,3,4-thiadiazol-2-yl]amino]-3-oxopropionate.

Melting point: 162°–166° C.

Nuclear magnetic resonance spectrum (in $CDCl_3$, TMS internal standard, ppm): 1.00(t,3H), 1.4–2.0(2H), 2.58(s,3H), 2.6–2.9(2H), 3.71(s,2H), 3.77(s,3H), 4.46(s,2H), 5.14(s,2H), 6.7–7.0(3H), 7.2–7 4(2H), 7.52(d,1H), 12.3(1H), 2.7(s,1H)

EXAMPLE 7

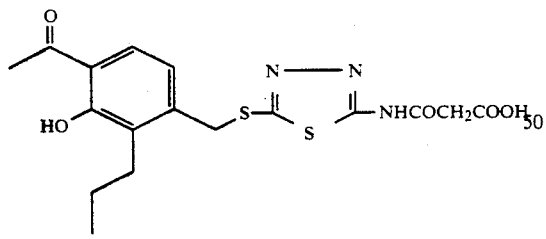

Using as a starting material 0.27 g of p-methoxybenzyl 3-[[5-[(4-acetyl-3-hydroxy-2-propylbenzyl)thio]-1,3,4-thiadiazol-2-yl]amino]-3-oxopropionate obtained in Example 6, 0.16 g of 3-[[5-[(4-acetyl-3-hydroxy-2-propylbenzyl)thio]1,3,4-thiadiazol-2-yl]amino]-3-oxo-pripionic acid was obtained in a manner similar to Example 2.

Melting point: 184°–187° C.

Nuclear magnetic resonance spectrum (in $DMSO-d_6$, TMS internal standard, ppm): 0.93(t,3H), 1.3–1.7(2H), 2.5–2.8(2H), 2.63(s,3H), 3.0–3.8(2H), 3.53(s,2H), 4.54(s,2H), 6.96(d,1H), 7.74(d,1H), 12.73(s,1H)

EXAMPLE 8

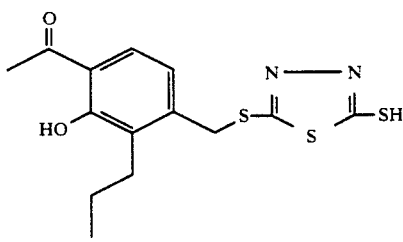

To a mixture of 0.30 g of 4-acetyl-3-hydroxy-2-propylbenzyl chloride, 0.24 g of 2,5-dimercapto-1,3,4-thiadiazole, 0.20 g of anhydrous potassium carbonate and 4 ml of methyl ethyl ketone was added a catalytic amount of tetra-n-butylammonium bromide. The mixture was stirred at 60° C. for 1 hour. After the reaction solution was rendered neutral by adding diluted hydrochloric acid thereto, it was extracted with ethyl acetate. After the extract was dried over anhydrous magnesium sulfate, the solvent was distilled off. The residue was recrystallized from isopropyl alcohol to give 0.20 g of 2-[(4-acetyl-3-hydroxy-2-propylbenzyl)thio]-5-mercapto-1,3,4-thiadiazole.

The obtained crystals were applied to silica gel column chromatography. By eluting with a mixture of hexaneethyl acetate (5:1), 0.03 g of the above-described product having a higher purity was obtained Melting point: 133°–135° C.

| Elemental analysis (as $C_{14}H_{16}N_2O_2S_3$) | | | | |
|---|---|---|---|---|
| | C (%) | H (%) | N (%) | S (%) |
| Calcd. | 49.39 | 4.74 | 8.23 | 28.25 |
| Found | 49.41 | 4.60 | 8.17 | 28.19 |

EXAMPLE 9

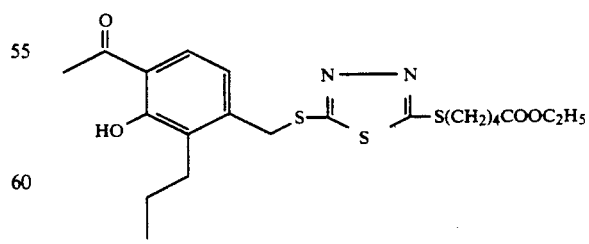

To a mixture of 0.30 g of 4-acetyl-3-hydroxy-2-propylbenzyl chloride, 0.39 g of ethyl 5-[(5-mercapto-1,3,4-thiadiazol-2-yl)thio]valerate, 0.20 g of anhydrous potassium carbonate and 4 ml of methyl ethyl ketone were added catalytic amounts of potassium iodide and tetran-butylammonium bromide followed by stirring at 60° C. for 3 hours The reaction mixture was diluted with ethyl acetate and insoluble matters were filtered off. The filtrate was washed with an aqueous sodium hydroxide solution and dried over anhydrous magnesium sulfate. The solvent was then distilled off. The residue was applied to silica gel column chromatography. Elution with a mixture of hexane-ethyl acetate (5:1) gave 0.52 g of oily ethyl 5-[[5-[(4-acetyl-3-hydroxy-2-propylbenzyl)thio]-1,3,4-thiadiazol-2-yl]thio]valerate.

Nuclear magnetic resonance spectrum (in CDCl₃, TMS internal standard, ppm): 0.99(t,3H), 1.25(t,3H), 1.4-1.7(2H), 1.7-2.0(4H), 2.34(t,2H), 2 61(s,3H), 2.5-2.8(2H), 3.30(t,2H), 4.12(q,2H), 4.56(s,2H), 6.94(d,1H), 7.54(d,1H), 12.68(s,1H)

Mass spectrum m/z: 468 (M⁺)

EXAMPLE 10

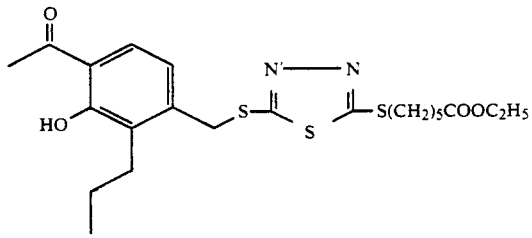

Using as starting materials 0.30 g of 4-acetyl-3-hydroxy-2-propylbenzyl chloride and 0.46 g of ethyl 6-[(5-mercapto-1,3,4-thiadiazol-2-yl]thio]hexanate, 0 59 g of oily ethyl 6-[[5-[(4-acetyl-3-hydroxy-2-propylbenzyl)thio]-1,3,4-thiadiazol-2-yl]thio]hexanate was obtained in a manner similar to Example 9.

Nuclear magnetic resonance spectrum (in CDCl₃, TMS internal standard, ppm): 0.99(t,3H), 1.25(t,3H), 1.3-2.0(8H), 2.30(t,2H), 2 62(s,3H), 2.5-2.8(2H), 3.28(t,2H), 4.12(q,2H), 4.57(s,2H), 6.93(d,1H), 7.54(d,1H), 12.68(s,1H)

Mass spectrum m/z: 482 (M⁺)

EXAMPLE 11

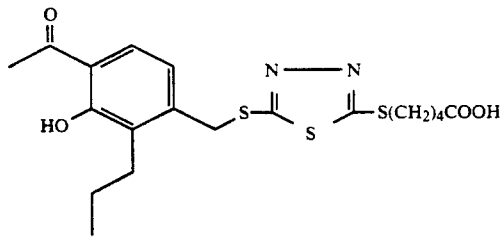

In 2 ml of 90% methanol was dissolved 0.20 g of ethyl 5-[[5-[(4-acetyl-3-hydroxy-2-propylbenzyl)thio]-1,3,4-thiadiazol-2-yl]thio]valerate obtained in Example 9 with heating at 60° C. Further 1.5 ml of a 1N aqueous sodium hydroxide solution was added to the solution followed by stirring at 60° C. for 30 minutes. An aqueous sodium hydroxide solution and ethyl acetate were added to the reaction solution to fractionate. The aqueous phase was made acidic with 2N hydrochloric acid and extracted with ethyl acetate. The extract was washed with, in sequence, water, a saturated aqueous sodium chloride solution and then water and, dried over anhydrous magnesium sulfate. The solvent was then distilled off to give 0.18 g of oily 5-[[5-[(4-acetyl-3-hydroxy-2-propylbenzyl)thio]-1,3,4-thiadiazol-2-yl]thio]valeric acid.

Nuclear magnetic resonance spectrum (in DMSO-d₆. TMS internal standard, ppm): 1.00(t.3H), 1.3-1.9(6H), 2.24(t,2H), 2.63(s,3H), 2.4-2.8(2H), 3.27(t,2H), 4.58(s,2H), 7.00(d,1H), 7.76(d,1H), 12.05(s,1H), 12.73(s,1H)

Mass spectrum m/z: 440 (M⁺)

EXAMPLE 12

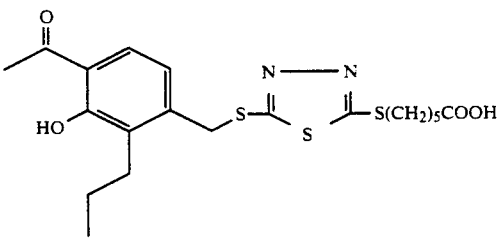

Ethyl 6-[[5-[(4-acetyl-3-hydroxy-2-propylbenzyl)thio]-1,3,4-thiadiazol-2-yl]thio]hexanate, 0.29 g, obtained in Example 10 as a starting material was treated in a manner similar to Example 11. The thus obtained solid was recrystallized from isopropyl alcohol to give 0.02 g of 6-[[5-[(4-acetyl-3-hydroxy-2-propylbenzyl)thio]-1,3,4-thiadiazol-2-yl]thio]hexanoic acid.

Melting point: 67°-74° C.

| Elemental analysis (as $C_{20}H_{26}N_2O_4S_3$) | | | | |
|---|---|---|---|---|
| | C (%) | H (%) | N (%) | S (%) |
| Calcd. | 52.84 | 5.76 | 6.16 | 21.16 |
| Found | 52.54 | 5.59 | 6.14 | 21.09 |

EXAMPLE 13

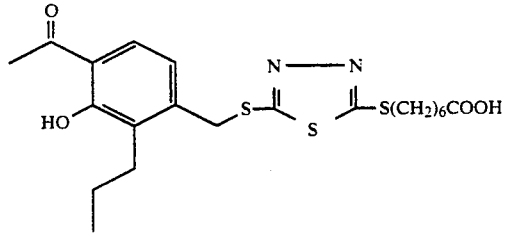

To a mixture of 0.20 g of 2-[(4-acetyl-3-hydroxy-2-propylbenzyl)thio]-5-mercapto-1,3,4-thiadiazole obtained in Example 8, 0.15 g of 7-bromoheptanoic acid, 0.18 g of anhydrous potassium carbonate and 5 ml of methyl ethyl ketone was added a catalytic amount of tetra-n-butylammonium bromide. The mixture was stirred at 60° C. for 1 hour. An aqueous sodium hydroxide solution and ethyl acetate were added to the reaction solution to perform fractionation. The aqueous phase was made acidic with 2N hydrochloric acid and extracted with ethyl acetate. After the extract was dried over anhydrous magnesium sulfate, the solvent was distilled off. The residue was applied to silica gel column chromatography. Elution with a mixture of hexane-ethyl acetate (2:1) gave 0.20 g of 7-[[5-[(4-acetyl-3-hydroxy-2-propylbenzyl)thio]-1,3,4-thiadiazol-2-yl]thio]heptanoic acid.

Melting point 63°-68° C.

| Elemental analysis (as $C_{21}H_{28}N_2O_4S_3$) | | | |
|---|---|---|---|
| | C (%) | H (%) | N (%) | S (%) |
| Calcd. | 53.82 | 6.02 | 5.98 | 20.53 |
| Found | 53.95 | 6.19 | 5.88 | 20.35 |

EXAMPLE 14

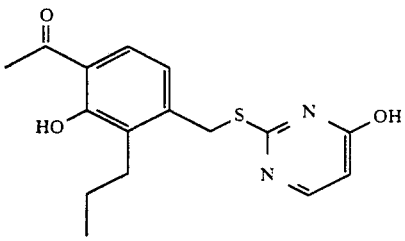

To a mixture of 0.30 g of 4-acetyl-3-hydroxy-2-propylbenzyl chloride, 0 20 g of 4-hydroxy-2-mercaptopyrimidine, 0.20 g of anhydrous potassium carbonate and 4 ml of methyl ethyl ketone was added a catalytic amount of tetra-n-butylammonium bromide. The mixture was stirred at 60° C. for 1 day.

A 1N aqueous sodium hydroxide solution and ethyl acetate were added to the reaction mixture to fractionate. The organic phase was dried over anhydrous magnesium sulfate, the solvent was distilled off. The residue was applied to silica gel column chromatography. Elution with a mixture of hexane-ethyl acetate (1:2) gave 0.10 g of 2-[(4-acetyl-3-hydroxy-2-propylbenzyl)thio]-4-hydroxypyrimidine.

Melting point: 177° C.

| Elemental analysis (as $C_{16}H_{18}N_2O_3S$) | | | |
|---|---|---|---|
| | C (%) | H (%) | N (%) | S (%) |
| Calcd. | 60.36 | 5.70 | 8.80 | 10.07 |
| Found | 60.33 | 5.70 | 8.63 | 9.90 |

EXAMPLE 15

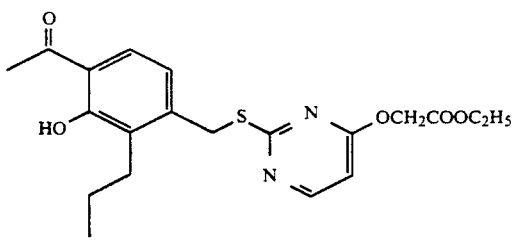

To a mixture of 0.06 g of 2-[(4-acetyl-3-hydroxy-2-propylbenzyl)thio]-4-hydroxypyrimidine obtained in Example 14, 0.06 g of ethyl bromoacetate, 0.04 g of anhydrous potassium carbonate and 3 ml of methyl ethyl ketone was added a catalytic amount of tetra-n-butylammonium bromide. The mixture was stirred at 60° C. for 1 hour. Water was added to the reaction mixture The resultant mixture was extracted with ethyl acetate. After the extract was dried over anhydrous magnesium sulfate, the solvent was distilled off. The residue was applied to silica gel column chromatography. Elution with a mixture of hexane-ethyl acetate (6:1) gave 0.06 g of ethyl [[2-[(4-acetyl-3-hydroxy-2-propylbenzyl)thio]-pyrimidin-4-yl]oxy]acetate.

Melting point: 112°–117° C.

Nuclear magnetic resonance spectrum (in $CDCl_3$, TMS internal standard, ppm): 1.00(t,3H), 1.25(t,3H), 1.4–1.8(2H), 2.59(s,3H), 2.5–2 9(2H), 4.22(q,2H), 4.38(s,2H), 4.87(s,2H), 6.56(d,1H), 6.94(d,1H), 7.53(d,1H), 8.30(d,1H), 2.7(s,1H)

Mass spectrum m/z: 404 ($M^+$)

EXAMPLE 16

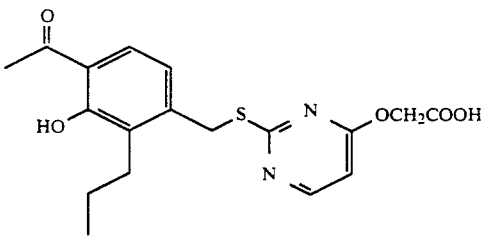

In 2 ml of 90% methanol was dissolved 0.06 g of ethyl [[2-[(4-acetyl-3-hydroxy-2-propylbenzyl)thio]-pyrimidin-4-yl]oxy]acetate obtained in Example 15 with heating at 60° C. Further 1 ml of a 1N aqueous sodium hydroxide solution was added to the solution followed by stirring at 60° C. for 15 minutes. An aqueous sodium hydroxide solution and ethyl acetate were added to the reaction mixture to fractionate. The aqueous phase was made acidic with 2N hydrochloric acid and extracted with ethyl acetate. The extract was washed with water and then dried over anhydrous magnesium sulfate The solvent was then distilled off. The thus obtained solid was recrystallized from isopropyl alcohol to give 0.02 g of [[2-[(4-acetyl-3-hydroxy-2-propylbenzyl)thio]-pyrimidin-4-yl]oxy]acetic acid.

Melting point: 174°–178° C.

| Elemental analysis (as $C_{18}H_{20}N_2O_5S$) | | | |
|---|---|---|---|
| | C (%) | H (%) | N (%) | S (%) |
| Calcd. | 57.43 | 5.36 | 7.44 | 8.52 |
| Found | 57.20 | 5.28 | 7.28 | 8.42 |

EXAMPLE 17

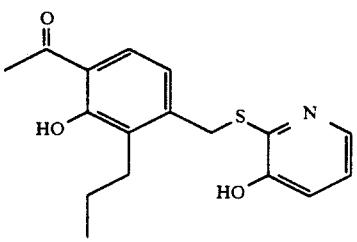

Using as starting materials 0.30 g of 4-acetyl-3-hydroxy-2-propylbenzyl chloride and 0.25 g of 3-hydroxy-2-mercaptopyridine, 0.33 g of 2-[(4-acetyl-3-hydroxy-2-propylbenzyl)thio]-3-hydroxypyridine was obtained in a manner similar to Example 14.

Melting point: 126° C.

| Elemental analysis (as C₁₇H₁₉NO₃S) | | | | |
|---|---|---|---|---|
| | C (%) | H (%) | N (%) | S (%) |
| Calcd. | 64.33 | 6.03 | 4.41 | 10.10 |
| Found | 64.16 | 5.95 | 4.43 | 9.96 |

EXAMPLE 18

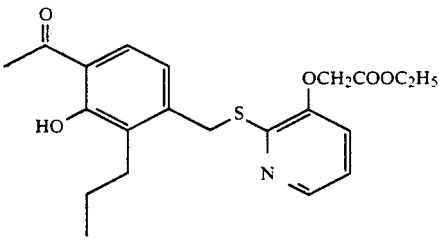

Using as starting materials 0.10 g of 2-[(4-acetyl-3-hydroxy-2-propylbenzyl)thio]-3-hydroxypyridine was obtained in Example 17 and 0.07 g of ethyl bromoacetate, 0.09 g of ethyl [[2-[(4-acetyl-3-hydroxy-2-propylbenzyl)thio]pyridin-3-yl]-oxy]acetate was obtained in a manner similar to Example 15.

Melting point: 98°–100° C.

| Elemental analysis (as C₂₁H₂₅NO₅S) | | | | |
|---|---|---|---|---|
| | C (%) | H (%) | N (%) | S (%) |
| Calcd. | 62.51 | 6.24 | 3.47 | 7.95 |
| Found | 62.29 | 6.14 | 3.42 | 8.06 |

EXAMPLE 19

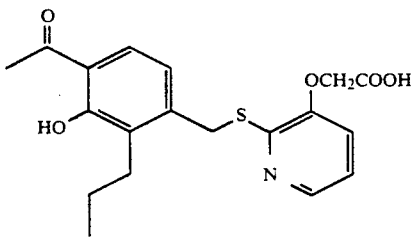

Using as a starting material 0.07 g of ethyl [[2-[(4-acetyl-3-hydroxy-2-propylbenzyl)thio]pyridin-3-yl]oxy]acetate obtained in Example 18, 0.02 g of [[2-[(4-acetyl-3-hydroxy-2-propylbenzyl)thio]pyridin-3-yl]oxy]acetic acid was obtained in a manner similar to Example 16.

Melting point: 157° C.

| Elemental analysis (as C₁₉H₂₁NO₅S) | | | | |
|---|---|---|---|---|
| | C (%) | H (%) | N (%) | S (%) |
| Calcd. | 60.78 | 5.64 | 3.73 | 8.54 |
| Found | 60.66 | 5.61 | 3.70 | 8.63 |

The following compounds were prepared in a manner similar to Example 14.

EXAMPLE 20

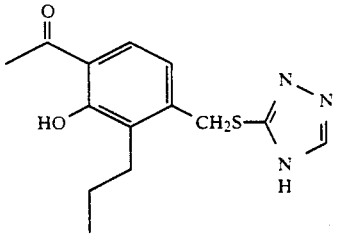

Using 3-mercapto-1,2,4-4H-triazole and 4-acetyl-3-hydroxy-2-propylbenzyl chloride, 2-hydroxy-3-propyl-4-[[(1,2,4-4H-triazol-3-yl)thio]methyl]acetophenone was obtained.

Melting point: 150°–151° C.

| Elemental analysis (as C₁₄H₁₇N₃O₂S) | | | | |
|---|---|---|---|---|
| | C (%) | H (%) | N (%) | S (%) |
| Calcd. | 57.71 | 5.88 | 14.42 | 11.09 |
| Found | 57.76 | 5.84 | 14.50 | 10.84 |

EXAMPLE 21

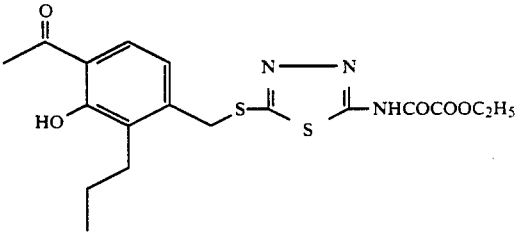

To a solution of 0.30 g of 2-amino-5-[(4-acetyl-3-hydroxy-2-propylbenzyl)thio]-1,3,4-thiadiazole obtained in Example 5 in 6.5 ml of pyridine was dropwise added 0.20 g of ethyloxalyl chloride at −30° C. The mixture was stirred at room temperature for 30 minutes. Water was added to the reaction mixture followed by extraction with ethyl acetate. After the extract was dried over anhydrous magnesium sulfate, the solvent was distilled off The residue was subjected to silica gel column chromatography Elution with a solvent mixture of chloroform-ethyl acetate (8:1) gave 0.15 g of ethyl [5-[(4-acetyl-3-hydroxy-2-propylbenzyl)thio]-1,1,4-thiadiazol-2-yl]oxamate Melting point: 189° C.

Nuclear magnetic resonance spectrum (in CDCl₃, TMS internal standard, ppm): 1.00(t,3H), 1.44(t,3H), 1.3–1.8(2H), 2.59(s,3H), 2.6–2.9(2H), 4.46(q,2H), 4.54(s,2H), 6.92(d,1H), 7.52(d,1H), 12.67(s,1H)

Mass spectrum m/z: 423 (M⁺)

EXAMPLE 22

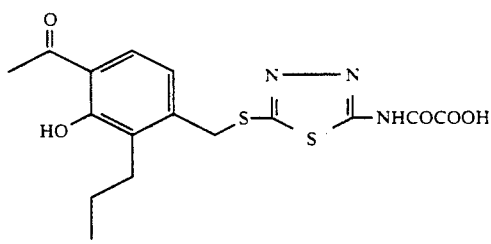

In 8 ml of 90% methanol was suspended 0.14 g of ethyl [5-[(4-acetyl-3-hydroxy-2-propylbenzyl)thio]1,3,4-thiadiazol-2-yl]oxamate obtained in Example 21. Further 2 ml of a 1N aqueous sodium hydroxide solution was added to the suspension followed by stirring at room temperature for 20 minutes. An aqueous sodium hydroxide solution and ethyl acetate were added to the reaction mixture to fractionate. The aqueous phase was made acidic with 1N hydrochloric acid and extracted with ethyl acetate After the extract was dried over anhydrous magnesium sulfate, the solvent was distilled off. The residue was recrystallized from isopropyl alcohol. The resultant crystals were dissolved in an aqueous sodium hydroxide solution 1N Hydrochloric acid was added to the solution to render acidic. The precipitated solid was taken by filtration and dried under reduced pressure to give 0.02 g of [5-[(4-acetyl-3-hydroxy-2-propylbenzyl)thio]-1,3,4-thiadiazol-2-yl]oxamidic acid.

Melting point: 208° C. (decomposed)

Nuclear magnetic resonance spectrum (in DMSO-$d_6$, TMS internal standard, ppm): 0.94(t,3H), 1.3–1.8(2H), 2.64(s,3H), 2.5–2 8(2H), 4.56(s,2H), 6.98(d,1H), 7.85(d,1H), 12.74(s,1H)

Mass spectrum m/z: 396 ((M+H)$^+$)

EXAMPLE 23

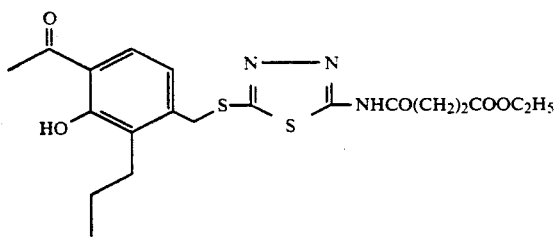

Using as starting materials 0.20 g of 2-amino-5-[(4-acetyl-3-hydroxy-2-propylbenzyl)thio]-1,3,4-thiadiazole and 0.15 g of ethyl succinyl chloride, 0.28 g of ethyl 4-[[5-[(4-acetyl-3-hydroxy-2-propylbenzyl) thio]-1,3,4-thiadiazol-2-yl]-amino]-4-oxobutyrate was obtained in a manner similar to Example 21.

Melting point: 166° C.

Nuclear magnetic resonance spectrum (in CDCl$_3$, TMS internal standard, ppm): 0.99(t,3H), 1.23(t,3H), 1.4–1.9(2H), 2.62(s,3H), 2 6–2 9(4H), 2.9–3 2(2H), 4.13(q,2H), 4 50(s,2H), 6.90(d,1H), 7.53(d,1H), 12.69(s,1H)

Mass spectrum m/z: 451 (M$^+$)

EXAMPLE 24

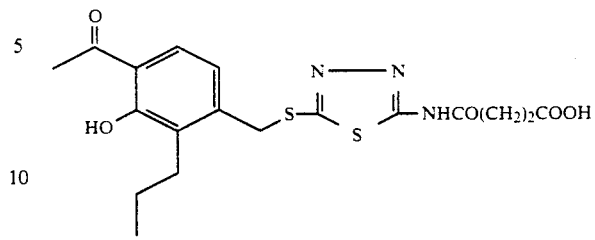

In 8 ml of 90% methanol was suspended 0.27 g of ethyl [[5-[(4-acetyl-3-hydroxy-2-propylbenzyl)thio]-1,3,4-thiadiazol-2-yl]amino]-4-oxobutyrate obtained in Example 23. Further 2 ml of a 1N aqueous sodium hydroxide solution was added to the suspension followed by stirring at room temperature for 20 minutes. An aqueous sodium hydroxide solution and ethyl acetate were added to the reaction mixture to fractionate. The aqueous phase was made acidic with a 1N hydrochloric acid and extracted with ethyl acetate After the extract was dried over anhydrous magnesium sulfate, the solvent was distilled off. The residue was recrystallized from isopropyl alcohol to give 0.11 g of 4-[[5-[(4-acetyl-3-hydroxy-2-propylbenzyl)thio]-1,3,4-thiadiazol-2-yl]amino]-4-oxobutyric acid.

Melting point: 194° C. (decomposed)

| Elemental analysis (as $C_{18}H_{21}N_3O_5S_2$) | | | |
|---|---|---|---|
| | C (%) | H (%) | N (%) | S (%) |
| Calcd. | 51.05 | 5.00 | 9.92 | 15.14 |
| Found | 51.11 | 5.08 | 9.75 | 14.92 |

Reference Example 1 (starting material of Example 25)

Cl(CH$_2$)$_3$SCH$_2$COOC$_2$H$_5$

A mixture of 2.00 g of ethyl mercaptoacetate, 3.13 g of 1-bromo-3-chloropropane, 2.29 g of anhydrous potassium carbonate and 10 ml of N,N-dimethylformamide was stirred at room temperature for 3 hours. The reaction mixture was diluted with toluene and insoluble matters were filtered off. The filtrate was washed with an aqueous sodium hydroxide solution and water, in this sequence After drying over anhydrous magnesium sulfate, the solvent was distilled off. The residue was applied to silica gel column chromatography. Elution with a solvent mixture of hexane-ethyl acetate (15:1) gave 2.65 g of oily ethyl [(3-chloropropyl)thio]acetate.

Nuclear magnetic resonance spectrum (in CDCl$_3$, TMS internal standard, ppm): 1.28(t,3H), 1.9–2.2(2H), 2.7–2 9(2H), 3.20(s,3H), 3.64(t,2H), 4.19(q,2H)

Mass spectrum m/z: 196 (M$^+$)

Reference Example 2 (starting material of Example 26)

(a)

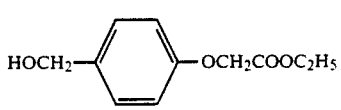

To a mixture of 2.00 g of p-hydroxybenzyl alcohol, 3.23 g of ethyl bromoacetate, 2.45 g of anhydrous potassium carbonate and 15 ml of N,N-dimethylformamide was added tetra-n-butylammonium bromide in a catalytic amount. The mixture was stirred at room temperature for 3 hours. The reaction mixture was diluted with ethyl acetate and insoluble matters were filtered off. The filtrate was washed with an aqueous sodium hydroxide solution and water, in this sequence. After drying over anhydrous magnesium sulfate, the solvent was distilled off. The residue was applied to silica gel column chromatography. Elution with a solvent mixture of hexaneethyl acetate (3:2) gave 2.16 g of oily ethyl [p-(hydroxymethyl)phenoxy]acetate.

Nuclear magnetic resonance spectrum (in CDCl$_3$,

TMS internal standard, ppm): 1.27(t,3H), 1.6-1.8(1H), 4.25(q,2H), 4.58(s,2H), 4.60(d,2H), 6.8-7.0(2H), 7.2-7.4(2H)

Mass spectrum m/z: 210 (M$^+$)

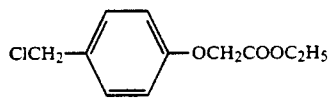

(b)

To a solution of 0.30 g of ethyl [p-(hydroxymethyl)phenoxy]acetate obtained in (a) above in 3 ml of benzene was dropwise added 0.13 ml of thionyl chloride. The mixture was stirred at room temperature for 1 hour. The reaction mixture was diluted with toluene and chilled water was added thereto to fractionate. After the organic layer was dried over anhydrous magnesium sulfate, the solvent was distilled off. The residue was applied to silica gel column chromatography. Elution with a solvent mixture of hexane-ethyl acetate (6:1) gave 0.31 g of oily ethyl [p-(chloromethyl)phenoxy]acetate. Nuclear magnetic resonance spectrum (in CDCl$_3$, TMS internal standard, ppm): 1.29(t,3H), 4.26(q,2H), 4.54(s,2H), 4.60(s,2H) 6.8-7.0(2H), 7.2-7.4(2H)

Mass spectrum m/z: 228 (M$^+$)

Reference Example 3 (starting material of Example 27)

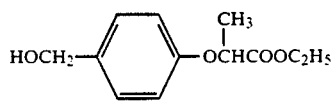

(a)

Using as starting materials 1 00 g of p-hydroxybenzyl alcohol and 1.61 g of ethyl 2-bromopropionate, 1.44 g of ethyl 2-[p-(hydroxymethyl)phenoxy]propionate was obtained in a manner similar to Reference Example 2.

Nuclear magnetic resonance spectrum (in CDCl$_3$,

TMS internal standard, ppm): 1.22(t,3H), 1.59(d,3H), 1.6-1.8(1H), 4.19(q,2H), 4.59(d,2H), 4.73(q,1H), 6.8-7.0(2H), 7.2-7.4(2H)

Mass spectrum m/z: 224 (M$^+$)

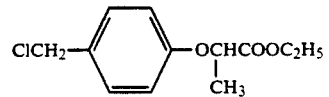

(b)

Using as a starting material 1.39 g of 2-[p-(hydroxymethyl)phenoxy]propionate obtained in (a) above, 1.33 g of ethyl 2-[p-(chloromethyl)phenoxy]propionate was obtained in a manner similar to Reference Example 2 (b).

Nuclear magnetic resonance spectrum (in CDCl$_3$.

TMS internal standard, ppm): 1.23(t,3H), 1.60(d,3H), 4.20(q,2H), 4.52(s,2H), 4.72(q,1H), 6.7-7.0(2H) 7.1-7.4(2H)

Mass spectrum m/z: 242 (M$^+$)

Reference Example 4 (starting material of Example 28)

To 4 ml of an aqueous solution of 0.39 g of sodium metaperiodate was added 3 ml of a methanol solution of 0.30 g of ethyl [(3-chloropropyl)thio]acetate obtained in Reference Example 1. The mixture was stirred at room temperature for 100 minutes To the reaction mixture was added 30 ml of a saturated aqueous sodium chloride solution followed by extraction with ethyl acetate The extract was dried over anhydrous magnesium sulfate The solvent was then distilled off. The residue was applied to silica gel column chromatography. Elution with a solvent mixture of hexaneethyl acetate (1:3) gave 0.31 g of ethyl (3-chloropropylsulfinyl)acetate.

Melting point: 46°-47° C.

| Elemental analysis (as C$_7$H$_{13}$O$_3$SCl) | | | | |
| --- | --- | --- | --- | --- |
| | C (%) | H (%) | S (%) | Cl (%) |
| Calcd. | 39.53 | 6.16 | 15.08 | 16.67 |
| Found | 39.25 | 6.42 | 15.04 | 16.78 |

Reference Example 5 (starting material of Example 29)

To a solution of 0.30 g of ethyl [(3-chloropropyl)-thio]acetate obtained in Reference Example 1 in 2 ml of acetic acid was added 1 ml of a 30% aqeuous hydrogen peroxide solution at 0° C. The mixture was stirred at 70° C. for 1 hour.

To the reaction mixture was added 40 ml of a saturated aqueous sodium hydrogen carbonate solution followed by extraction with ethyl acetate. The extract was washed with, in sequence, a saturated hydrogen sodium carbonate aqueous solution, a 10% hydrogen sodium sulfite aqueous solution and water. After drying over anhydrous magnesium sulfate, the solvent was distilled off. The residue was applied to silica gel column chromatography. Elution with a solvent mixture of hexane-ethyl acetate (2:1) gave 0.30 g of oily ethyl (3-chloropropylsulfonyl)acetate.

Nuclear mangetic resonance spectrum (in CDCl$_3$,

TMS internal standard, ppm): 1.37(t,3H), 2.2-2.5(2H), 3.4-3.6(2H), 3.71(t,3H), 4.01(s,2H), 4.29(q,2H)

Mass spectrum m/z: 229 ((M+1)$^+$)

EXAMPLE 25

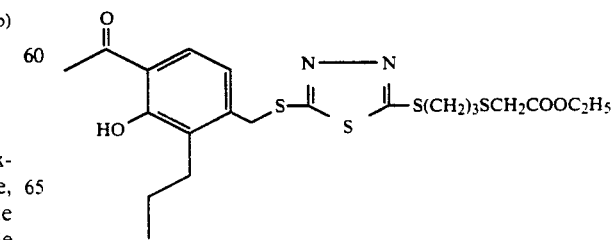

To a mixture of 0.20 g of 2-[(4-acetyl-3-hydroxy-2-propylbenzyl)thio]-5-mercapto-1,3,4-thiadiazole obtained in Example 8, 0.14 g of ethyl [(3-chloropropyl)-thio]acetate obtained in Reference Example 1, 0.09 g of anhydrous potassium carbonate and 5 ml of N,N-dimethylformamide was added tetra-n-butylammonium bromide in a catalytic amount followed by stirring at 60° C. for 10 hours. The reaction mixture was diluted with toluene and insoluble matters were filtered off. The filtrate was washed with an aqueous sodium hydroxide solution and water in this sequence. After drying over anhydrous magnesium sulfate, the solvent was removed by distillation. The residue was applied to silica gel column chromatography. Elution with a solvent mixture of hexane–ethyl acetate (5:1) gave 0.15 g of oily ethyl [[3-[[5-[(4-acetyl-3-hydroxy-2-propylbenzyl)thio]-1,3,4-thiadiazol-2-yl]-thio]propyl]thio]acetate.

Nuclear magnetic resonance spectrum (in CDCl₃, TMS internal standard, ppm): 0.99(t,3H), 1.26(t,3H), 1.4–1.8(2H), 1.9–2.3(2H), 2.58(s,3H), 2.6–2.9(4H), 3.19(s,2H), 3.40(t,2H), 4.18(s,2H), 4.54(s,2H), 6.93(d,1H), 7.54(d,1H), 12.67(s,1H)

Mass spectrum m/z: 500 (M⁺)

EXAMPLE 26

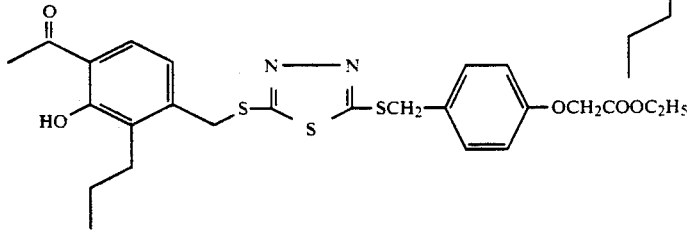

To a mixture of 0.20 g of 2-[(4-acetyl-3-hydroxy-2-propylbenzyl)thio]-5-mercapto-1,3,4-thiadiazole, 0.16 g of ethyl [(p-chloromethyl)phenoxy]acetate obtained in Reference Example 2, 0.09 g of anhydrous potassium carbonate and 4 ml of 2-butanone was added a catalytic amount of tetra-n-butyl ammonium bromide. The mixture was stirred at 60° C. for 30 hours. The reaction mixture was diluted with ethyl acetate and insoluble matters were filtered off. The filtrate was washed with, in sequence, an aqueous sodium hydroxide solution and water. After drying over anhydrous magnesium sulfate, the solvent was distilled off. The residue was subjected to silica gel column chromatography. Elution with a solvent mixture of hexane-ethyl acetate (4:1) gave 0.21 g of oily ethyl [p-[[[5-[(4-acetyl-3-hydroxy-2-propylbenzyl)-thio]-1,3,4-thiadiazol-2-yl]thio]methyl]phenoxy-]acetate.

Nuclear magnetic resonance spectrum (in CDCl₃, TMS internal standard, ppm): 1.00(t,3H) 1.29(t,3H), 1.4–1.8(2H), 2.63(s,3H), 2.6–2.8(2H) 4.27(q,2H), 4.47(s,2H) 4.56(s,2H), 4.61(s,2H), 6.8–7.0,7.2–7.4(2H), 7.54(d,1H), 12.7(s,1H) Mass spectrum m/z: 532 (M⁺)

EXAMPLE 27

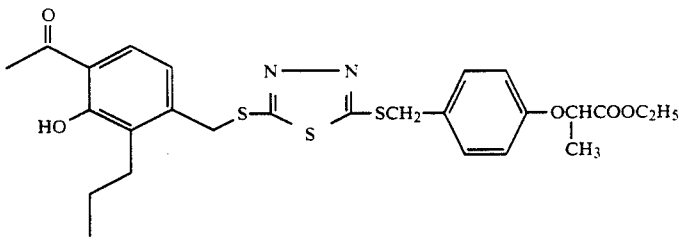

Using as starting materials 0.20 g of 2-[(4-acetyl-3-hydroxy-2-propylbenzyl)thio]-5-mercapto -1,3,4-thiadiazole and 0.17 g of ethyl 2-[(p-chloromethyl)-phenoxy]propionate obtained in Reference Example 3, 0.23 g of ethyl 2-[p-[[[5-[(4-acetyl-3-hydroxy-2-propylbenzyl) thio]-1,3,4-thiadiazol-2-yl]thio]methyl]phenoxy]propionate was obtained in a manner similar to Example 26.

Nuclear magnetic resonance spectrum (in CDCl3, TMS internal standard, ppm): 0.99(t,3H), 1.22(t,3H), 1.4–1.8(2H), 1.59(d,3H), 2.58(s,3H), 2.6–2.9(2H), 4.20(q,1H), 4.44(s,2H), 4.54(s,2H), 4.70(q,1H), 6.7–7.0(3H), 7.2–7.4(2H), 7.53(d,1H) 12.67(s,1H)

Mass spectrum m/z: 546 (M⁺)

EXAMPLE 28

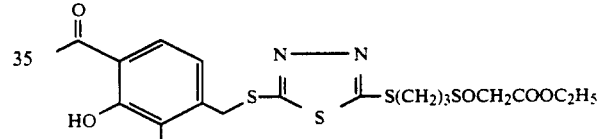

Using as starting materials 0.24 g of 2-[(4-acetyl-3-hydroxy-2-propylbenzyl)thio]-5-mercpato -1,3,4-thiadiazole and 0.18 g of ethyl (3-chloropropylsulfinyl-)acetate obtained in Reference Example 4, 0.22 g of oily ethyl [3-[[5-[(4-acetyl-3-hydroxy-2-propylbenzyl)thio]-1,3,4-thiadiazol-2-yl]thio]propylsulfinyl]acetate was obtained in a manner similar to Example 25.

Nuclear magnetic resonance spectrum (in CDCl₃, TMS internal standard, ppm): 1.00(t,3H), 0.30(t,3H), 1.4–1.8(2H), 2.2–2.6(2H), 2.60(s,3H), 2.6–2.9(2H), 2.9–3.2(2H), 3.48(t,2H), 3.70(s,2H), 4.25(q,2H), 4.55(s,2H), 6.94(d,1H), 7.55(d,1H), 12.68(s,1H)

Mass spectrum m/z: 516 (M⁺)

EXAMPLE 29

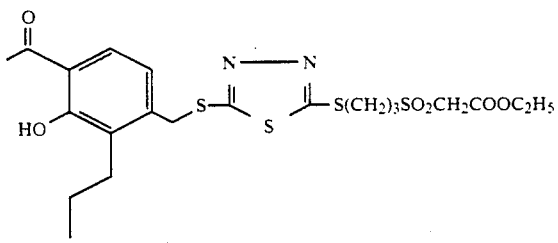

Using as starting materials 0.25 g of 2-[(4-acetyl-3-hydroxy-2-propylbenzyl)thio]-5-mercapto-1,3,4-thiadiazole and 0.20 g of ethyl (3-chloropropylsulfonyl)acetate obtained in Reference Example 5, 0.21 g of oily ethyl [3-[[5-[[(4-acetyl-3-hydroxy-2-propylbenzyl)thio]-1,3,4-thiadiazol-2-yl]thio]-propylsulfonyl]acetate was obtained in a manner similar to Example 25.

Nuclear magnetic resonance spectrum (in CDCl$_3$,

TMS internal standard, ppm): 1.00(t,3H), 1.31(t,3H), 1.4–1.8(2H), 2.3–2.9(4H), 2.60(s,3H), 3.3–3.7(4H), 3.98(s,2H), 4.27(q,2H), 4.59(s,2H), 6.93(d,1H), 7.55(d,1H), 12.68(s,1H)

Mass spectrum m/z: 533 ((M+1)$^+$)

EXAMPLE 30

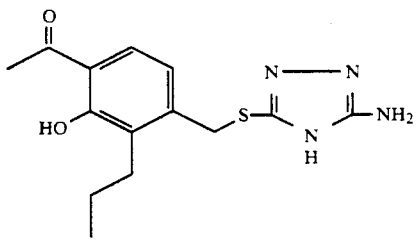

Using 0.30 g of 4-acetyl-3-hydroxy-2-propylbenzyl chloride and 0.18 g of 3-amino-5-mercapto-1,2,4-triazole as starting materials, 0.25 g of 4'-[[(5-amino-1,2,4-triazol-3-yl]thio]methyl]-2'-hydroxy-3'-propylacetophenone was obtained in a manner similar to Example 25.

Nuclear magnetic resonance spectrum (in CDCl$_3$-DMSO-d$_6$,

TMS internal standard, ppm): 0.99(t,3H), 1.3–1.8(2H), 2.59(s,3H), 2.6–2.8(2H), 4.28(s,2H), 4.8–5.3(2H), 6.92(d,1H), 7.53(d,1H) 11 5(1H), 12 (1H)

Mass spectrum m/z: 306 (M$^+$)

EXAMPLE 31

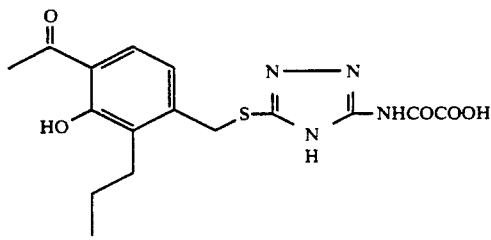

In 3 ml of pyridine was dissolved 0.15 g of 4'-[[(5-amino-1,2,4-triazol-3-yl]thio]methyl]-2'-hydroxy-3'-propylacetophenone obtained in Example 30. To the solution was added 0.31 g of ethyloxalyl chloride at 0° C. The mixture was stirred at room temperature for 1 hour. Chilled water was added to the reaction mixture followed by extraction with ethyl acetate After washing with 1N hydrochloric acid and water sequentially, the extract was dried over anhydrous magnesium sulfate. The solvent was then distilled off. The resulting white solid was suspended in 5 ml of 90% methanol and, 4 ml of a 1N aqueous sodium hydroxide solution was added to the solution followed by stirring at room temperature for 2 hours. An aqueous sodium hydroxide solution and ethyl acetate were added to the reaction mixture to fractionate. The aqueous phase was made acidic with 2N hydrochloric acid. The precipitated white solid was taken by filtration and dried under reduced pressure to give 0.14 g of N-[[5-[(4-acetyl-3-hydroxy-2-propylbenzyl)thio]-1,2,4-triazol-3-yl]amino]oxamic acid.

Melting point: 220° C. (decomposed)

| Elemental analysis (as C$_{16}$H$_{18}$N$_4$O$_5$S) | | | |
|---|---|---|---|
| C (%) | H (%) | N (%) | S (%) |
| Calcd. 50.79 | 4.79 | 14.81 | 8.47 |
| Found 50.84 | 4.80 | 14.54 | 8.46 |

EXAMPLE 32

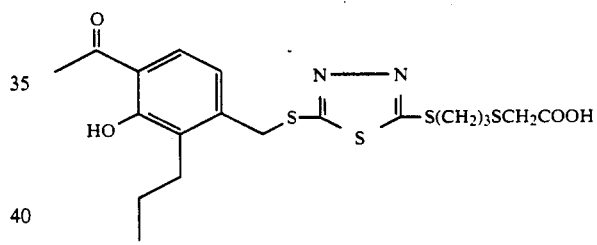

In 2 ml of 90% methanol was suspended 0.14 g of ethyl [[3-[[5-[(4-acetyl-3-hydroxy-2-propylbenzyl)thio]-1,3,4-thiadiazol-2-yl]thio]propyl]thio]acetate obtained in Example 25. Further 1 ml of a 1N aqueous sodium hydroxide solution was added to the suspension followed by stirring at room temperature for 45 minutes. An aqueous sodium hydroxide solution and ethyl acetate were added to the reaction mixture to fractionate. The aqueous phase was made acidic with 1N hydrochloric acid and extracted with ethyl acetate. After the extract was washed with water and then dried over anhydrous magnesium sulfate, the solvent was distilled off. The residue was applied to silica gel column chromatography. Elution with a solvent mixture of hexane-ethyl acetate (1:2) gave 0.14 g of oily [[3-[[5-[(4-acetyl-3-hydroxy-2-propylbenzyl)thio]-1,3,4-thiadiazol-2-yl]thio]propyl]thio]acetic acid.

Nuclear magnetic resonance spectrum (in CDCl$_3$,

TMS internal standard, ppm): 1.00(t,3H), 1.3–1.8(2H), 1.9–2.4(2H), 2.59(s,3H), 2.6–3.0(4H), 3.26(s,2H), 3.40(t,2H), 4.54(s,2H), 4.8–5.0(1H), 6.92(d,1H), 7.54(d,1H) 12 67(s,1H)

Mass spectrum m/z: 472 (M$^+$)

EXAMPLE 33

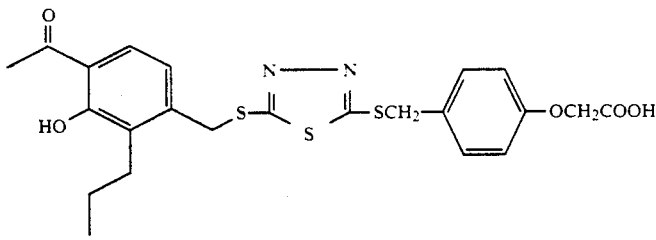

In 2 ml of 90% methanol was suspended 0.20 g of ethyl [p-[[[5-[(4-acetyl-3-hydroxy-2-propylbenzyl)thio]-1,3,4-thiadiazol-2-yl]thio]methyl]phenoxy]acetate obtained in Example 26. Further 1 ml of a 1N aqueous sodium hydroxide solution was added to the suspension followed by stirring at room temperature for 1 minute. An aqueous sodium hydroxide solution and ethyl acetate were added to the reaction mixture to fractionate. The aqueous phase was made acidic with a 1N hydrochloric acid and extracted with ethyl acetate. After the extract was washed with water and dried over anhydrous magnesium sulfate, the solvent was distilled off. The resultant solids were recrystallized from isopropyl alcohol to give 0.15 g of [p-[[[5-[(4-acetyl-3-hydroxy-2-propylbenzyl)thio]-1,3,4-thiadiazol-2-yl]thio]methyl]phenoxy]acetic acid.

Melting point: 131°-134° C.

| Elemental analysis (as $C_{23}H_{24}N_2O_5S_3$) | | | |
|---|---|---|---|
| | C (%) | H (%) | N (%) | S (%) |
| Calcd. | 54.74 | 4.79 | 5.55 | 19.06 |
| Found | 54.45 | 4.74 | 5.35 | 18.89 |

EXAMPLE 34

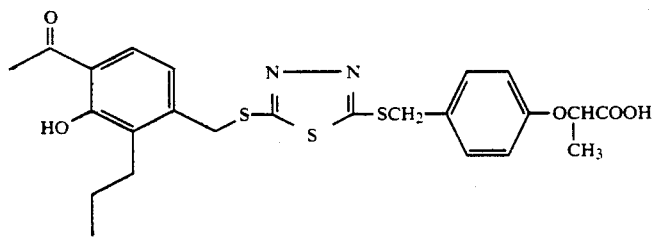

Using as a starting material 0.22 g of 2-[p-[[[5-[(4-acetyl-3-hydroxy-2-propylbenzyl)thio]-1,3,4-thiadiazol-2-yl]-thio]methyl]phenoxy]propionate obtained in Example 27, 0.11 g of 2-[p-[[[5-[(4-acetyl-3-hydroxy-2-propylbenzyl)thio]-1,3,4-thiadiazol-2-yl]thio]methyl]phenoxy]propionic acid was obtained in a manner similar to Example 33.

Melting point: 138°-142° C.

| Elemental analysis (as $C_{24}H_{26}NO_5S_3$) | | | |
|---|---|---|---|
| | C (%) | H (%) | N (%) | S (%) |
| Calcd. | 55.58 | 5.05 | 5.40 | 18.55 |
| Found | 55.54 | 5.04 | 5.32 | 18.55 |

EXAMPLE 35

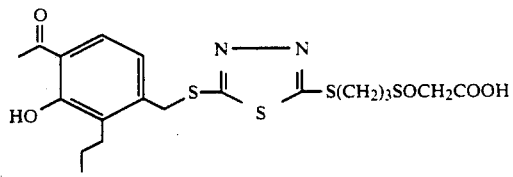

Using as a starting material 0.20 g of ethyl [3-[[5-[(4-acetyl-3-hydroxy-2-propylbenzyl)thio]-1,3,4-thiadiazol-2-yl]thio]propylsulfinyl]acetate obtained in Example 28, 0.16 g of [3-[[5-[(4-acetyl-3-hydroxy-2-propylbenzyl)thio]1,3,4-thiadiazol-2-yl]thio]propylsulfinyl]acetic acid was obtained in a manner similar to Example 33.

Melting point: 107°-110° C.

| Elemental analysis (as $C_{19}H_{24}N_2O_5S_4$) | | | |
|---|---|---|---|
| | C (%) | H (%) | N (%) | S (%) |
| Calcd. | 46.70 | 4.95 | 5.73 | 26.25 |
| Found | 46.56 | 5.23 | 5.47 | 26.04 |

EXAMPLE 36

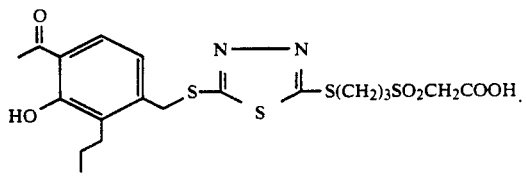

Using as a starting material 0.19 g of ethyl [3-[[5-[(4-acetyl-3-hydroxy-2-propylbenzyl)thio]-1,3,4-thiadiazol-2-yl]thio]propylsulfonyl]acetate obtained in Example 29, 0.13 g of [3-[[5-[(4-acetyl-3-hydroxy-2-propylbenzyl]thio]-1,3,4-thiadiazol-2-yl]thio]propylsulfonyl]acetic acid was obtained in a manner similar to Example 33.

Melting point: 122°-125° C.

| Elemental analysis (as $C_{19}H_{24}N_2O_6S_4$) | | | |
|---|---|---|---|
| | C (%) | H (%) | N (%) | S (%) |
| Calcd. | 45.22 | 4.79 | 5.55 | 25.42 |
| Found | 45.09 | 4.99 | 5.38 | 25.60 |

EXAMPLE 37

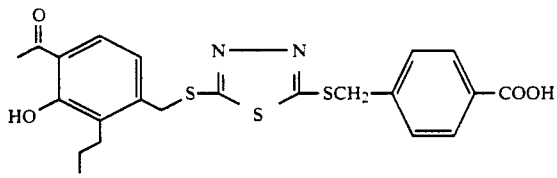

To a mixture of 0.49 g of 2-[(4-acetyl-3-hydroxy-2-propylbenzyl)thio]-5-mercapto-1,3,4-thiadiazole, 0.36 g of p-(bromomethyl)benzoic acid, 0.48 g of anhydrous potassium carbonate and 12 ml of 2-butanone was added a catalytic amount of tetra-n-butyl ammonium bromide followed by stirring at 60° C. for 45 minutes. An aqueous sodium hydroxide solution and ethyl acetate were added to the reaction mixture to fractionate. The aqueous phase was made acidic with 1N hydrochloric acid and extracted with ethyl acetate. The extract was washed with water and dried over anhydrous magnesium sulfate, the solvent was distilled off. The thus obtained solid was recrystallized from isopropyl alcohol to give 0.50 g of p-[[5-[(4-acetyl-3-hydroxy-2-propylbenzyl)-thio]-1,3,4-thiadiazol-2-yl]thiomethyl]benzoic acid.

Melting point: 163°-166° C.

| Elemental analysis (as $C_{22}H_{22}N_2O_4S_3$) | | | |
|---|---|---|---|
| | C (%) | H (%) | N (%) | S (%) |
| Calcd. | 55.67 | 4.79 | 5.90 | 20.27 |
| Found | 55.63 | 4.65 | 5.73 | 20.14 |

REFERENCE EXAMPLE 6

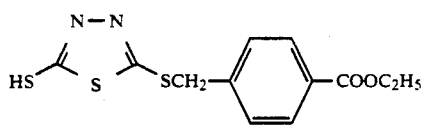

To a mixture of 1.2 g of 2,5-dimercapto-1,3,4-thiadiazole, 1.1 g of anhydrous potassium carbonate and 10 ml of N,N-dimethylformamide was added 0.5 g of ethyl p-(bromomethyl)benzoate followed by stirring at room temperature for 3 hours. The reaction mixture was made acidic with diluted hydrochloric acid and extracted with ethyl acetate. The extract was washed with water, dried over anhydrous magnesium sulfate and concentrated under reduced pressure. The residue was applied to silica gel column chromatography followed by eluting with a solvent mixture of toluene-ethyl acetate (9:1). The thus obtained crystals were recrystallized from toluene-n-hexane to give 230 mg of ethyl p-[(5-mercapto-1,3,4-thiadiazol-2-yl)thiomethyl]benzoate.

Melting point: 114°-115° C.

| Elemental analysis (as $C_{12}H_{12}N_2O_2S_3$) | | | |
|---|---|---|---|
| | C (%) | H (%) | N (%) | S (%) |
| Calcd. | 46.13 | 3.87 | 8.97 | 30.79 |
| Found | 46.20 | 3.84 | 8.81 | 30.89 |

REFERENCE EXAMPLE 7

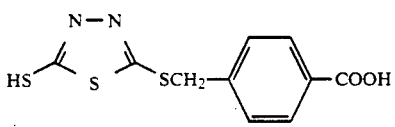

To a mixture of 1.5 g of 2,5-dimercapto-1,3,4-thiadiazole, 2.76 g of anhydrous potassium carbonate and 10 ml of N,N-dimethylformamide was added 1 g of p-(bromomethyl)benzoic acid followed by stirring at room temperature for 3 hours. The reaction mixture was diluted with 30 ml of water, made acidic with diluted hydrochloric acid and, extracted with ethyl acetate. The extract was washed with water, dried over anhydrous magnesium sulfate and concentrated under reduced pressure. The residue was applied to silica gel column chromatography. Elution with a mixture of toluene-ethyl acetate (1:1) gave 400 mg of p-[(5-mercapto-1,3,4-thiadiazol-2-yl)thiomethyl]benzoic acid.

Melting point: 230°-232° C.

| Elemental analysis (as $C_{10}H_8N_2O_2S_3$) | | | |
|---|---|---|---|
| | C (%) | H (%) | N (%) | S (%) |
| Calcd. | 42.24 | 2.84 | 9.85 | 33.82 |
| Found | 42.18 | 2.91 | 9.68 | 33.86 |

EXAMPLE 38

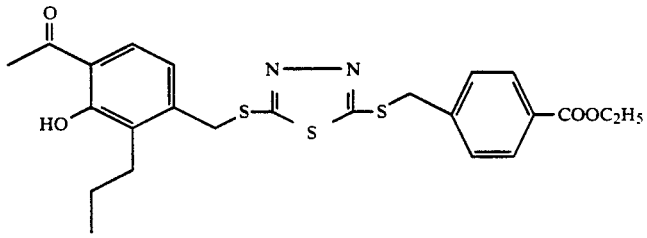

To a mixture of 340 mg of 2-[(4-acetyl-3-hydroxy-2-propylbenzyl)thio]-5-mercapto-1,3,4-thiadiazole, 150 mg of anhydrous potassium carbonate and 5 ml of N,N-dimethylformamide was added 220 mg of ethyl p-(bromomethyl)benzoate followed by stirring at room temperature for 3 hours. The reaction mixture was diluted with 30 ml of toluene. After washing with water and drying over anhydrous magnesium sulfate, the system was concentrated under reduced pressure. The residue was applied to silica gel column chromatography. Elution with a mixture of toluene-ethyl acetate (9:1) gave 0.38 g of oily ethyl p-[[5-[(4-acetyl-3-hydroxy-2-propylbenzyl)thio]-1,3,4-thiadiazol-2-yl]thiomethyl]benzoate.

Nuclear magnetic resonance spectrum (in CDCl₃.

TMS internal standard, ppm): 1.0(t,3H), 1.59(t,3H), 1.2-1.9(m,4H), 2.62(s,3H) 2.6-2.8(m,2H), 4.37(q,2H), 4.54(s,2H) 4.56(s,2H), 6.92(d,1H), 7.51(dd,4H), 8.0(d,1H), 12.69(s,1H)

EXAMPLE 39

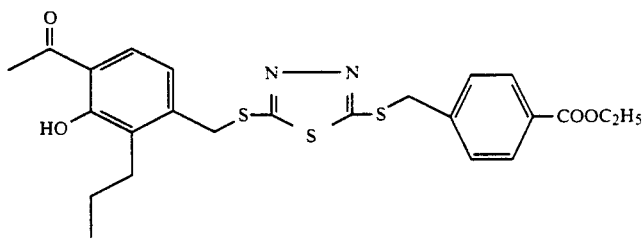

To a mixture of 230 mg of ethyl p-[(5-mercapto-1,3,4-thiadiazol-2-yl)thiomethyl]benzoate obtained in Reference Example 6, 110 mg of anhydrous potassium carbonate and 5 ml of N,N-dimethylformamide was added 160 mg of 4-acetyl-3-hydroxy-2-propylbenzyl chloride. The mixture was stirred at room temperature for 3 hours. To the reaction mixture was added 30 ml of toluene. The mixture was washed with water, dried over anhydrous magnesium sulfate and then concentrated under reduced pressure. The residue was applied to silica gel column chromatography. Elution with a mixture of toluene-ethyl acetate (9:1) gave 330 mg of oily ethyl p-[[5-[(4-acetyl-3-hydroxy-2-propylbenzyl)-thio]-1,3,4-thiadiazol-2-yl]thiomethyl]benzoate. The physical property of the thus obtained compound was identical with that of the compound obtained in Example 38.

EXAMPLE 40

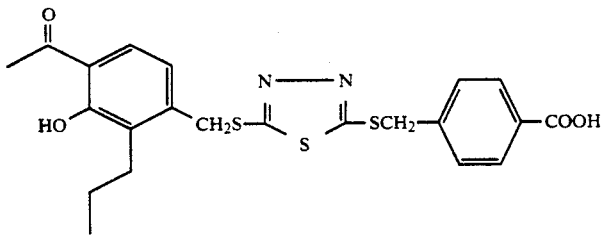

To a mixture of 200 mg of p-[(5-mercapto-1,3,4-thiadiazol-2-yl)thiomethyl]benzoic acid obtained in Reference Example 7, 200 mg of anhydrous potassium carbonate and 5 ml of N,N-dimethylformamide was added 170 mg of 4-acetyl-3-hydroxy-2-propylbenzyl chloride. The mixture was stirred at room temperature for 2 hours. The reaction mixture was diluted with 20 ml of water, washed with ethyl acetate, made acidic with dil. hydrochloric acid and then extracted with ethyl acetate. The extract was washed with water, dried over anhydrous magnesium sulfate and then concentrated under reduced pressure. The residue was recrystallized from isopropyl alcohol to give 130 mg of p-[[5-[(4-acetyl-3-hydroxy-2-propylbenzyl)thio]-1,3,4-thiadiazol-2-yl]thiomethyl]benzoic acid. The physical property of the thus obtained compound was identical with that of the compound obtained in Example 37.

EXAMPLE 41

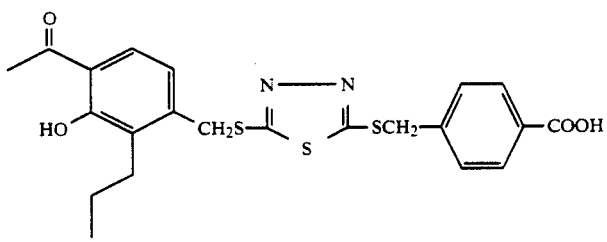

A mixture of 380 mg of ethyl p-[(5-[(4-acetyl-3-hydroxy-2-propylbenzyl )thio]-1,3,4-thiadiazol -2-yl)thiomethyl]benzoate, 2 ml of methanol, 2 ml of tetrahydrofuran and 2 ml of a 1N aqueous sodium hydroxide solution was stirred at 60° to 70° C. for 1 hour. After cooling, 20 ml cf water was added to the reaction mixture. The system was washed with ethyl acetate, made acidic with dil. hydrochloric acid and then, extracted with ethyl acetate. The extract was washed with water, dried over anhydrous magnesium sulfate and then concentrated under reduced pressure. The residue was recrystallized from isopropyl alcohol-water to give 100 mg of p-[[5-[(4-acetyl-3-hydroxy-2-propylbenzyl)thio]-1,3,4-thiadiazol-2-yl]thiomethyl]benzoic acid. The physical property of the thus obtained compound was identical with that of the compound obtained in Example 37.

REFERENCE EXAMPLE 8

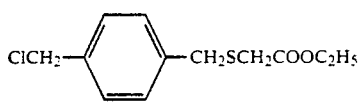

To a mixture of 1.22 g of ethyl thioglycolate, 1.4 g of anhydrous potassium carbonate and 20 ml of N,N-dimethylformamide was added 5.3 g of p-xylene dichloride followed by stirring at room temperature overnight. To the reaction mixture was added 50 ml of toluene. The mixture was washed with water, dried over anhydrous magnesium sulfate and concentrated under reduced pressure. The residue was applied to silica gel column chromatography. Elution with a mixture of toluene-ethyl acetate (9:1) gave 1.61 g of oily ethyl [(p-chloromethylbenzyl)thio]acetate.

Nuclear magnetic resonance spectrum (in CDCl$_3$, TMS internal standard, ppm): 1.28(t,3H), 3.05(s,2H), 3.82(s,2H), 4.18(q,2H), 4.56(s,2H), 7.33(s,4H)

EXAMPLE 42

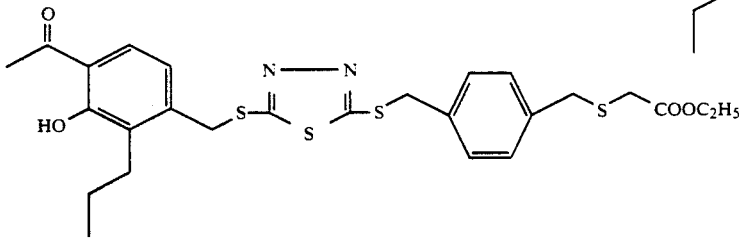

To a mixture of 100 mg of 2-[(4-acetyl-3-hydroxy-2-propylbenzyl)thio]-5-mercapto-1,3,4-thiadiazole, 50 mg of anhydrous potassium carbonate and 5 ml of N,N-dimethylformamide was added 90 mg of ethyl [(p-chloromethyl)benzyl)thio]-acetate obtained in Reference Example 8 followed by stirring at room temperature for 3 hours. To the reaction mixture was added 30 ml of toluene. The mixture was washed with water, dried over anhydrous magnesium sulfate and concentrated under reduced pressure. The residue was applied to silica gel column chromatography. Elution with a mixture of tolueneethyl acetate (9:1) gave 100 mg of oily ethyl [[p-[[[5-[(4-acetyl-3-hydroxy-2-propylbenzyl)thio]-1,3,4-thiadiazol-2-yl]-thio]methyl]benzyl]thio]acetate.

Nuclear magnetic resonance spectrum (in CDCl$_3$, TMS internal standard, ppm): 1.00(t,3H), 1.28(t,3H), 1.40-1.80(m,2H), 2.60(s,3H), 2.50-2.84(m,2H), 3.04(s,2H), 3.81(s,2H), 4.18(q,2H), 4.50(s,2H), 4.56(s,2H), 6.94(d,1H), 7.31(s,2H), 7.34(s,2H), 7.55(d,1H), 12.67(s,1H)

EXAMPLE 43

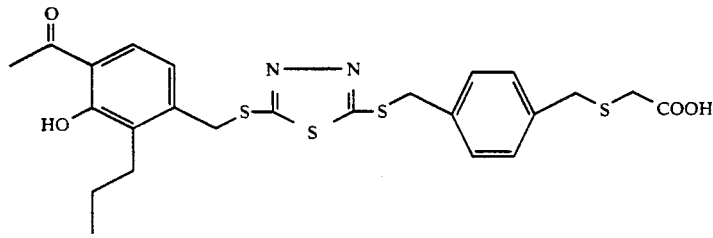

In a manner similar to Example 41, 50 mg of [[p-[[[5-[(4-acetyl-3-hydroxy-2-propylbenzyl)thio]-1,3,4-thiadiazol-2-yl]thio]methyl]benzyl]thio]acetic acid was obtained except for using 100 mg of ethyl [[p-[[[5-[(4-acetyl-3-hydroxy-2-propylbenzyl)thio]1,3,4-thiadiazol-2-yl]-thio]methyl]benzyl]thio]acetic acid obtained in Example 42 as a starting material.

Melting point: 102°-104° C.

| Elemental analysis (as C$_{24}$H$_{26}$N$_2$O$_4$S$_4$) | | | | |
|---|---|---|---|---|
| | C (%) | H (%) | N (%) | S (%) |
| Calcd. | 53.91 | 4.90 | 5.24 | 23.99 |
| Found | 54.02 | 5.03 | 5.23 | 23.81 |

EXAMPLE 44

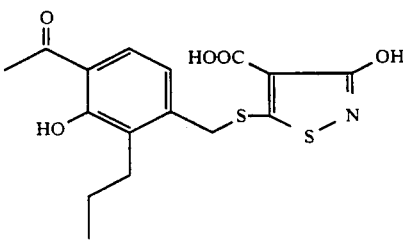

To a mixture of 0.20 g of 4-acetyl-3-hydroxy-2-propylbenzyl chloride, 0.19 g of tripotassium 3-oxide-5-sulfido-4-isothiazole carboxylate, 0.05 g of anhydrous potassium carbonate and 5 ml of 2-butanone was added a catalytic amount of tetra-n-butylammonium bromide. After stirring at 60° C. for 2 days, the mixture was treated as in Example 9 to give 0.04 g of 5-[(4-acetyl-3-hydroxy-2-propylbenzyl)thio]-3-hydroxy-4-isothiazolecarboxylic acid.

Melting point: 210° C. (decomposed)

Nuclear magnetic resonance spectrum (in DMSO-d$_6$, TMS internal standard, ppm): 0.94(t,3H), 1.3-1.8(2H), 2.64(s,3H), 2.5-2.8(2H), 4.32(s,2H), 7.08(d,1H), 7.80(d,1H), 12.75(s,1H)

Mass spectrum m/z: 367 (M$^+$)

REFERENCE EXAMPLE 9

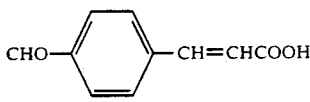

A drop of piperidine was added to a mixture of 13.4 g of p-tolualdehyde, 5 g of malonic acid and 50 ml of pyridine. The mixture was heated to reflux until evolution of carbon dioxide was discontinued. The reaction mixture was concentrated under reduced pressure and, 200 ml of water and 12 g of hydrogen sodium carbonate were added thereto. The mixture was washed with ethyl acetate and made acidic with conc. hydrochloric acid. The precipitated crystals were taken out by filtration, thoroughly washed with water and dried to give 6.6 g of p-formylcinnamic acid.

Melting point: higher than 250° C.

REFERENCE EXAMPLE 10

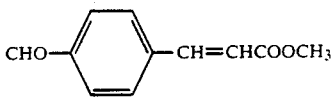

A mixture of 4 g of p-formylcinnamic acid obtained in Reference Example 9, 3.5 g of methyl iodide, 3.3 g of anhydrous potassium carbonate and 30 ml of N,N-dimethylformamide was stirred at room temperature overnight. The reaction mixture was diluted with 200 ml of toluene. After washing with a 5% sodium hydrogen carbonate aqueous solution and water, the system was dried over anhydrous magnesium sulfate and concentrated under reduced pressure to give 3.8 g of methyl p-formylcinnamate.

Melting point: 82°-84° C.

REFERENCE EXAMPLE 11

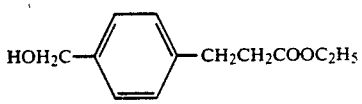

To a solution of 3.8 g of methyl p-formylcinnamate obtained in Reference Example 10 in 30 ml of ethanol and 10 ml of tetrahydrofuran was added 0.1 g of 10% palladiumcarbon. Catalytic reduction was performed at normal temperature under normal pressure until absorption of hydrogen was ceased. The catalyst was removed by filtration and, 1 g of sodium borohydride was added to the filtrate followed by stirring at room temperature overnight. The reaction mixture was concentrated under reduced pressure and 200 ml of ethyl acetate was added to the concentrate. The system was washed with water, dried over anhydrous magnesium sulfate and concentrated under reduced pressure to give 3.5 g of oily ethyl 3-(p-hydroxymethylphenyl)propionate.

Nuclear magnetic resonance spectrum (in $CDCl_3$, TMS internal standard, ppm): 1.20(t,3H), 2.4-2.76(m,2H), 2.76-3.10(m,2H), 4.10(q,2H), 4.62(brs,2H), 7.0-7.40(m,4H)

REFERENCE EXAMPLE 12

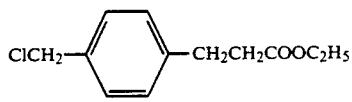

In a manner similar to Reference Example 8, 3.4 g of oily ethyl 3-(p-chloromethylphenyl)propionate was obtained except for using 3.5 g of ethyl 3-(p-hydroxymethylphenyl)-propionate obtained in Reference Example 11 as a starting material.

Nuclear magnetic resonance spectrum (in $CDCl_3$, TMS internal standard, ppm): 1.20(t,3H), 2.40-2.76(m,2H), 2.76-3.10(m,2H), 4.11(q,2H), 4.54(s,2H), 7.0-7.40(m,4H)

EXAMPLE 45

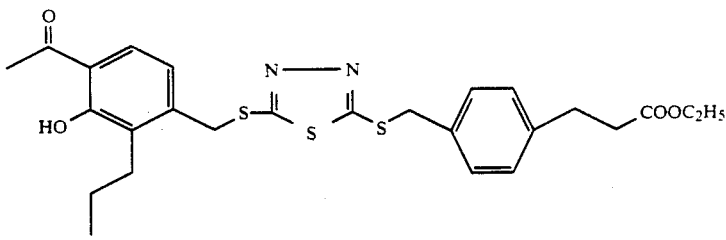

In a manner similar to Example 42, 160 mg of oily ethyl 3-[p-[[[5-[(4-acetyl-3-hydroxy-2-propylbenzyl)thio]-1,3,4-thiadiazol -2-yl]thio]methyl]phenyl]propionate was obtained except for using 130 mg of 2-[(4-acetyl-3-hydroxy-2-propylbenzyl)thio]-5-mercapto-1,3,4-thiadiazole obtained in Example 8 and 100 mg ethyl 3-(p-chloromethylphenyl)propionate obtained in Reference Example 12 as starting materials.

Nuclear magnetic resonance spectrum (in $CDCl_3$, TMS internal standard, ppm): 1.00(t,3H), 1.20(t,3H), 1.36-1.80(m,2H), 2.59(s,3H), 2.40-3.10(m,4H), 4.11(q,2H), 4.46(s,2H), 4.54(s,2H), 6.92(d,1H), 7.00-7.40(m,4H), 7.54(d,1H), 12.6(s,1H)

Mass spectrum m/z: 531 ($M^+ +1$)

EXAMPLE 46

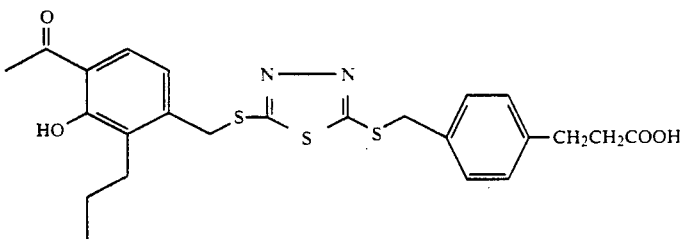

In a manner similar to Example 41, 120 mg of 3-[p-[[[5-[(4-acetyl-3-hydroxy-2-propylbenzyl)thio]-1,3,4-thiadiazol-2-yl]thio]methyl]phenyl]propionic acid was obtained except for using 160 mg of ethyl 3-[p-[[[5-[(4-acetyl-3-hydroxy-2-propylbenzyl)thio]-1,3,4-thiadiazol-2-yl]-thio]methyl]phenyl]propionate obtained in Example 45 as a starting material.

Nuclear magnetic resonance spectrum (in CDCl$_3$, TMS internal standard, ppm): 1.0(t,3H), 1.2-1.8(m,2H), 2.60(s,3H), 2.5-3.2(m,4H), 4.46(s,2H), 4.54(s,2H), 6.92(d,1H), 7.0-7.4(m,4H), 7.52(d,1H), 12.69(s,1H)

Mass spectrum m/z: 503 (M$^+$ +1)

EXAMPLE 47

| (Tablet) | |
|---|---|
| Compound of Example 37 | 30 mg |
| Lactose | 104 mg |
| Corn starch | 57 mg |
| Hydroxypropyl cellulose | 4 mg |
| Calcium carboxymethyl cellulose | 4 mg |
| Magnesium stearate | 1 mg |
| Total | 200 mg |

After uniformly mixing 30 g of Compound of Example 37, 104 g of lactose and 57 g of corn starch, 40 ml of a 10% (w/w) aqueous solution of hydroxypropyl cellulose was added to the mixture and the resulting mixture was granulated by a wet granulation method. The granules thus obtained were mixed with 4 g of calcium carboxymethyl cellulose and 1 g of magnesium stearate and the mixture was press-tabletted into tablet (200 mg per tablet).

EXAMPLE 48

| (Capsule) | |
|---|---|
| Compound of Example 37 | 30 mg |
| Crystalline cellulose | 40 mg |
| Crystalline lactose | 129 mg |
| Magnesium stearate | 1 mg |
| Total | 200 mg |

The above components each in an amount 1000 times the foregoing amount were mixed and then filled in gelatin capsule to provide capsules (200 mg per capsule).

EXAMPLE 49

(Inhalation)

After dissolving 0.1 g of Compound of Example 37 in about 90 ml of a mixture of ethanol, propylene glycol and purified water (30:10:60 in a weight ratio), the volume of the solution was adjusted to 100 ml using the aforesaid mixture and 10 ml each of the solution was filled in a definite container followed by sealing to provide an inhalation.

I claim:

1. A heterocyclic compound represented by the formula:

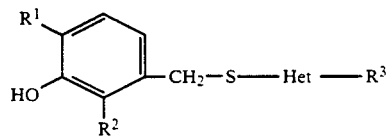

wherein $R^1$ represents a $C_1$-$C_6$ alkanoyl group; $R^2$ represents a lower alkyl group; Het represents a pyridine ring; $R^3$ represents a carboxy group, an amino group, a lower alkylamino group, a carboxy lower alkylamine group, a lower alkanoylamino group, a carboxy lower alkanoylamino group, a di-lower alkylamino group, a hydroxy group, a lower alkoxy group, a carboxy lower alkoxy group, a mercapto group, a lower alkylthio group, a carboxy lower alkylthio group, a group represented by the formulas:

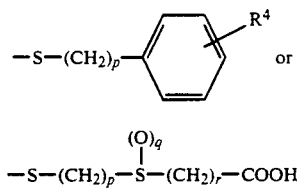

wherein p represents an integer of 1 to 5, q represents 0, 1 or 2, r represents an integer of 1 to 5; $R^4$ represents a carboxy group, a lower alkoxy group, a carboxy lower alkoxy group, a lower alkyl group, or a carboxyl lower alkyl group and each, except for the carboxy group, may have a sulfur atom or an oxygen atom between two carbon atoms in the carbon chain thereof); provided that when the compound is substituted by a carboxy group, said carboxy group may be in the form of a lower alkyl ester, a phenyl lower alkyl ester, a lower alkoxy phenyl lower alkyl ester, or a pharmacologically acceptable non-toxic acid addition salt.

2. A compound or a pharmacologically acceptable non-toxic acid addition salt according to claim 1, wherein $R^3$ is a group represented by the formula:

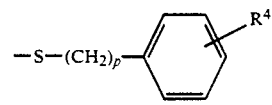

and wherein p, $R^1$,$R^2$,$R^4$ and n are as defined.

3. The compound or salt of claim 2 wherein $R^4$ is a carboxy group, an alkoxy group or a carboxy alkoxy group.

4. A pharmaceutical composition useful as an antagonist of SRS-A comprised of a therapeutically effective amount of the compound of claim 1 and a pharmaceutically acceptable carrier.

5. A method for antagonizing the effects of SRS-A in a host which comprises administering to said host a therapeutically effective amount of the composition of claim 4.

* * * * *